(12) United States Patent
Bayer et al.

(10) Patent No.: US 11,932,584 B2
(45) Date of Patent: Mar. 19, 2024

(54) METHOD OF FORMING A MYCOLOGICAL PRODUCT

(71) Applicant: Ecovative Design LLC, Green Island, NY (US)

(72) Inventors: Eben Bayer, Troy, NY (US); Gavin McIntyre, Troy, NY (US)

(73) Assignee: ECOVATIVE DESIGN LLC, Green Island, NY (US)

( * ) Notice: Subject to any disclaimer, the term of this patent is extended or adjusted under 35 U.S.C. 154(b) by 161 days.

(21) Appl. No.: 16/661,726

(22) Filed: Oct. 23, 2019

(65) Prior Publication Data

US 2020/0055274 A1 Feb. 20, 2020
US 2022/0396052 A9 Dec. 15, 2022

Related U.S. Application Data

(62) Division of application No. 13/856,086, filed on Apr. 3, 2013, now Pat. No. 10,525,662, which is a division of application No. 12/001,556, filed on Dec. 12, 2007, now Pat. No. 9,485,917.

(51) Int. Cl.
| | |
|---|---|
| C05D 9/00 | (2006.01) |
| A01G 18/00 | (2018.01) |
| A01G 18/40 | (2018.01) |
| A01G 18/50 | (2018.01) |
| A01G 18/64 | (2018.01) |
| B32B 5/02 | (2006.01) |
| B32B 5/16 | (2006.01) |
| C12N 1/14 | (2006.01) |
| C12N 11/14 | (2006.01) |

(52) U.S. Cl.
CPC ............... *C05D 9/00* (2013.01); *A01G 18/00* (2018.02); *A01G 18/40* (2018.02); *A01G 18/50* (2018.02); *A01G 18/64* (2018.02); *B32B 5/02* (2013.01); *B32B 5/16* (2013.01); *C12N 1/14* (2013.01); *C12N 11/14* (2013.01); *B32B 2439/00* (2013.01); *Y10T 428/1348* (2015.01); *Y10T 428/249921* (2015.04); *Y10T 428/31504* (2015.04)

(58) Field of Classification Search
CPC ........... C05D 9/00; C05F 11/00; A01G 18/40; A01G 18/50; B32B 2439/00; B32B 5/02; B32B 5/16; C12N 11/14; C12N 1/14; Y10T 428/1348; Y10T 428/249921; Y10T 428/31504
See application file for complete search history.

(56) References Cited

U.S. PATENT DOCUMENTS

| | | | |
|---|---|---|---|
| 1,979,176 | A | 10/1934 | Schicht |
| 2,509,984 | A | 5/1950 | Morrow |
| 2,657,647 | A | 11/1953 | Rapisarda |
| 2,723,493 | A | 11/1955 | Stoller |
| 2,815,621 | A | 12/1957 | Carter |
| 2,964,070 | A | 12/1960 | Linhardt |
| 3,268,606 | A | 8/1966 | Jaeger |
| 3,316,592 | A | 5/1967 | Forrest |
| 3,317,375 | A | 5/1967 | Molinet et al. |
| 3,421,554 | A | 1/1969 | Carter |
| 3,477,558 | A | 11/1969 | Fleischauer |
| 3,499,261 | A | 3/1970 | Hullhorst et al. |
| 3,708,952 | A | 1/1973 | Schulze et al. |
| 3,717,953 | A | 2/1973 | Kuhn et al. |
| 3,782,033 | A | 1/1974 | Hickerson |
| 3,810,327 | A | 5/1974 | Giansante |
| 3,828,470 | A | 8/1974 | Stoller |
| 3,885,048 | A | 5/1975 | Liggett |
| 3,911,141 | A | 10/1975 | Farr et al. |
| 3,961,938 | A | 6/1976 | Iizuka et al. |
| 4,027,427 | A | 6/1977 | Stoller et al. |
| 4,036,122 | A | 7/1977 | Langen |
| 4,038,807 | A | 8/1977 | Beardsley et al. |
| 4,063,383 | A | 12/1977 | Green |
| 4,073,956 | A | 2/1978 | Yates |
| 4,127,965 | A | 12/1978 | Mee |
| 4,136,767 | A | 1/1979 | Sarovich |
| 4,226,330 | A | 10/1980 | Butler |
| 4,233,266 | A | 11/1980 | Kummer |
| 4,263,744 | A | 4/1981 | Stoller |
| 4,265,915 | A | 5/1981 | MacLennan et al. |
| 4,294,929 | A | 10/1981 | Solomons et al. |

(Continued)

FOREIGN PATENT DOCUMENTS

| | | |
|---|---|---|
| CN | 1059662 A | 3/1992 |
| CN | 1273249 A | 11/2000 |

(Continued)

OTHER PUBLICATIONS

Bartnicki-Garcia, "Cell wall chemistry, morphogenesis, and taxonomy of fungi", Annual Review Microbiol. (1968) 22(1): 87-108.
Cha et al., "Biomimetic synthesis of ordered silica structures mediated by block copolypeptides". Nature (2000) 403(6767): 289-292.
Dugdale J. "This new surf company is making boards of mushrooms". Blog post—Jun. 25, 2015.
Halseide P., "Cutting brick the safe way". The Aberdeen Group (1988) Publication #M880354 in 2 pages.
Highland Woodworking, "Making Thin Lumber and Veneer Out of Ordinary Boards", Sales Website (2017) in 3 pages.

(Continued)

Primary Examiner — Blaine Lankford
(74) Attorney, Agent, or Firm — Knobbe, Martens, Olson & Bear, LLP

(57) ABSTRACT

The method grows a mycelial mass over a three-dimensional lattice such that a dense network of oriented hyphae is formed on the lattice. Growth along the lattice results in mycelium composite with highly organized hyphae strands and allows the design and production of composites with greater strength in chosen directions due to the organized nature of the supporting mycelia structure.

10 Claims, 5 Drawing Sheets

(56) References Cited

U.S. PATENT DOCUMENTS

| | | |
|---|---|---|
| 4,337,594 A | 7/1982 | Hanacek et al. |
| 4,370,159 A | 1/1983 | Holtz |
| 4,568,520 A | 2/1986 | Ackermann et al. |
| 4,620,826 A | 11/1986 | Rubio et al. |
| 4,716,712 A | 1/1988 | Gill |
| 4,722,159 A | 2/1988 | Watanabe et al. |
| 4,878,312 A | 11/1989 | Shimizu |
| 4,922,650 A | 5/1990 | Akao et al. |
| 4,960,413 A | 10/1990 | Sagar et al. |
| 5,021,350 A | 6/1991 | Jung et al. |
| 5,030,425 A | 7/1991 | Bowers-Irons et al. |
| 5,074,959 A | 12/1991 | Yamanaka et al. |
| 5,085,998 A | 2/1992 | Lebron et al. |
| 5,088,860 A | 2/1992 | Stockdale et al. |
| 5,123,203 A | 6/1992 | Hiromoto |
| 5,230,430 A | 7/1993 | Kidder |
| 5,306,550 A | 4/1994 | Nishiyama et al. |
| 5,335,770 A | 8/1994 | Baker et al. |
| 5,370,714 A | 12/1994 | Ogawa |
| 5,433,061 A | 7/1995 | Hutchinson et al. |
| 5,440,860 A | 8/1995 | Meli et al. |
| 5,475,479 A | 12/1995 | Hatakeyama et al. |
| 5,498,384 A | 3/1996 | Volk et al. |
| 5,503,647 A | 4/1996 | Dahlberg et al. |
| 5,511,358 A | 4/1996 | Morita et al. |
| 5,532,217 A | 7/1996 | Silver et al. |
| 5,569,426 A | 10/1996 | Le Blanc |
| 5,589,390 A | 12/1996 | Higuchi et al. |
| 5,590,489 A | 1/1997 | Hattori et al. |
| 5,598,876 A | 2/1997 | Zanini et al. |
| 5,606,836 A | 3/1997 | Insalaco et al. |
| 5,647,180 A | 7/1997 | Billings et al. |
| 5,681,738 A | 10/1997 | Beelman et al. |
| 5,682,929 A | 11/1997 | Maginot et al. |
| 5,685,124 A | 11/1997 | Jandl |
| 5,711,353 A | 1/1998 | Ichikawa et al. |
| 5,802,763 A | 9/1998 | Milstein |
| 5,854,056 A | 12/1998 | Dschida |
| 5,888,803 A | 3/1999 | Starkey |
| 5,897,887 A | 4/1999 | Haeberli |
| 5,919,507 A | 6/1999 | Beelman et al. |
| 5,944,928 A | 8/1999 | Seidner |
| 5,948,674 A | 9/1999 | Mankiewicz |
| 5,979,109 A | 11/1999 | Sartor et al. |
| 6,041,544 A | 3/2000 | Kananen et al. |
| 6,041,835 A | 3/2000 | Price |
| 6,073,388 A | 6/2000 | Kananen et al. |
| 6,098,677 A | 8/2000 | Wegman et al. |
| 6,112,504 A | 9/2000 | McGregor et al. |
| 6,143,549 A | 11/2000 | Lamar et al. |
| 6,197,573 B1 | 3/2001 | Suryanarayan et al. |
| 6,226,962 B1 | 5/2001 | Eason et al. |
| 6,300,315 B1 | 10/2001 | Liu |
| 6,306,921 B1 | 10/2001 | Al Ghatta et al. |
| 6,329,185 B1 | 12/2001 | Kofod et al. |
| 6,349,988 B1 | 2/2002 | Foster et al. |
| 6,402,953 B1 | 6/2002 | Gorovoj et al. |
| 6,425,714 B1 | 7/2002 | Waddell |
| 6,444,437 B1 | 9/2002 | Sporleder et al. |
| 6,471,993 B1 | 10/2002 | Shastri et al. |
| 6,475,811 B1 | 11/2002 | Babcock |
| 6,482,942 B1 | 11/2002 | Vittori |
| 6,491,480 B2 | 12/2002 | Waddell |
| 6,500,476 B1 | 12/2002 | Martin et al. |
| 6,523,721 B1 | 2/2003 | Nomoto et al. |
| 6,603,054 B2 | 8/2003 | Chen et al. |
| 6,620,614 B1 | 9/2003 | Luth et al. |
| 6,660,164 B1 | 12/2003 | Stover |
| 6,679,301 B2 | 1/2004 | Makino et al. |
| 6,726,911 B1 | 4/2004 | Jülich et al. |
| 6,737,065 B2 | 5/2004 | Song et al. |
| 7,043,874 B2 | 5/2006 | Wasser et al. |
| 7,073,306 B1 | 7/2006 | Hagaman |
| 7,122,176 B2 | 10/2006 | Stamets |
| 7,179,356 B2 | 2/2007 | Aksay et al. |
| 7,395,643 B2 | 7/2008 | Franchini et al. |
| 7,514,248 B2 | 4/2009 | Gower et al. |
| 7,573,031 B2 | 8/2009 | Behar et al. |
| 7,621,300 B2 | 11/2009 | Bonney et al. |
| 7,661,248 B2 | 2/2010 | Conti et al. |
| 7,754,653 B2 | 7/2010 | Hintz |
| 7,836,921 B2 | 11/2010 | Isomura et al. |
| 8,001,719 B2 | 8/2011 | Bayer et al. |
| 8,067,237 B2 | 11/2011 | Mooney et al. |
| 8,205,646 B2 | 6/2012 | Isomura et al. |
| 8,227,224 B2 | 7/2012 | Kalisz et al. |
| 8,227,233 B2 | 7/2012 | Kalisz et al. |
| 8,241,415 B2 | 8/2012 | Wantling et al. |
| 8,298,809 B2 | 10/2012 | Kalisz et al. |
| 8,298,810 B2 | 10/2012 | Rocco et al. |
| 8,313,939 B2 | 11/2012 | Kalisz et al. |
| 8,517,064 B2 | 8/2013 | Isomura et al. |
| 8,658,407 B2 | 2/2014 | Lyons et al. |
| 8,763,653 B2 | 7/2014 | Weigel et al. |
| 8,999,687 B2 | 4/2015 | Bayer et al. |
| 9,068,171 B2 | 6/2015 | Kelly et al. |
| 9,079,978 B2 | 7/2015 | Räsänen et al. |
| 9,085,763 B2 | 7/2015 | Winiski et al. |
| 9,253,889 B2 | 2/2016 | Bayer et al. |
| 9,332,779 B2 | 5/2016 | Marga |
| 9,394,512 B2 | 7/2016 | Bayer et al. |
| 9,469,838 B2 | 10/2016 | Schaak et al. |
| 9,485,917 B2 | 11/2016 | Bayer et al. |
| 9,555,395 B2 | 1/2017 | Araldi et al. |
| 9,714,180 B2 | 7/2017 | McIntyre et al. |
| 9,752,122 B2 | 9/2017 | Marga et al. |
| 9,795,088 B2 | 10/2017 | Bayer et al. |
| 9,801,345 B2 | 10/2017 | Bayer et al. |
| 9,803,171 B2 | 10/2017 | Bayer et al. |
| 9,879,219 B2 | 1/2018 | McIntyre et al. |
| 9,914,906 B2 | 3/2018 | Winiski et al. |
| 10,125,347 B2 | 11/2018 | Winiski |
| 10,144,149 B2 | 12/2018 | Araldi et al. |
| 10,154,627 B2 | 12/2018 | McIntyre et al. |
| 10,172,301 B2 | 1/2019 | McNamara et al. |
| 10,266,695 B2 | 4/2019 | Lucht et al. |
| 10,407,675 B2 | 9/2019 | Bayer et al. |
| 10,525,662 B2 * | 1/2020 | Bayer .................. B32B 5/16 |
| 10,533,155 B2 | 1/2020 | Kozubal et al. |
| 10,537,070 B2 | 1/2020 | Betts et al. |
| 10,575,579 B2 | 3/2020 | Egeland et al. |
| 10,577,579 B2 | 3/2020 | Kozubal et al. |
| 10,583,626 B2 | 3/2020 | Bayer et al. |
| 10,589,489 B2 | 3/2020 | Bayer et al. |
| 10,590,379 B2 | 3/2020 | Kozubal et al. |
| 10,687,482 B2 | 6/2020 | Ross et al. |
| 10,785,925 B2 | 9/2020 | McNamara et al. |
| 11,001,801 B2 | 5/2021 | Kozubal et al. |
| 11,015,168 B2 | 5/2021 | Kozubal et al. |
| 11,149,247 B2 | 10/2021 | Harney et al. |
| 11,261,420 B2 | 3/2022 | Kozubal et al. |
| 11,266,085 B2 | 3/2022 | Kaplan-Bie et al. |
| 11,272,726 B2 | 3/2022 | Macur et al. |
| 11,277,979 B2 | 3/2022 | Greetham et al. |
| 11,277,981 B2 | 3/2022 | Ross |
| 11,293,005 B2 | 4/2022 | Carlton et al. |
| 11,297,866 B2 | 4/2022 | Kozubal et al. |
| 11,343,979 B2 | 5/2022 | Mueller et al. |
| 11,359,074 B2 | 6/2022 | Kaplan-Bie et al. |
| 11,359,174 B2 | 6/2022 | Winiski et al. |
| 11,407,973 B2 | 8/2022 | Harney et al. |
| 11,420,366 B2 | 8/2022 | McIntyre et al. |
| 11,432,575 B2 | 9/2022 | Macur et al. |
| 11,459,541 B2 | 10/2022 | Harney et al. |
| 11,464,251 B2 | 10/2022 | Kozubal et al. |
| 11,466,245 B2 | 10/2022 | Harney et al. |
| 11,478,007 B2 | 10/2022 | Macur et al. |
| 11,505,779 B2 | 11/2022 | Kozubal et al. |
| 11,666,080 B2 | 6/2023 | Kozubal et al. |
| 2001/0012235 A1 | 8/2001 | Schuchardt |
| 2002/0110427 A1 | 8/2002 | Waddell |
| 2002/0131828 A1 | 9/2002 | Waddell |
| 2002/0131933 A1 | 9/2002 | Delmotte |
| 2003/0017565 A1 | 1/2003 | Echigo et al. |

(56) References Cited

U.S. PATENT DOCUMENTS

| | | |
|---|---|---|
| 2003/0056451 A1 | 3/2003 | Plsek et al. |
| 2003/0121201 A1 | 7/2003 | Dahlberg et al. |
| 2003/0157219 A1 | 8/2003 | Bijl et al. |
| 2003/0232895 A1 | 12/2003 | Omidian et al. |
| 2004/0000090 A1 | 1/2004 | Miller |
| 2004/0020553 A1 | 2/2004 | Amano |
| 2004/0166576 A1 | 8/2004 | Sadaie |
| 2004/0177585 A1 | 9/2004 | Vermette |
| 2004/0211721 A1 | 10/2004 | Stamets |
| 2005/0053778 A1 | 3/2005 | Hukkanen |
| 2005/0133536 A1 | 6/2005 | Kelsey et al. |
| 2005/0137272 A1 | 6/2005 | Gaserod et al. |
| 2006/0121006 A1 | 6/2006 | Chancellor et al. |
| 2006/0134265 A1 | 6/2006 | Beukes |
| 2006/0280753 A1 | 12/2006 | McNeary |
| 2007/0079944 A1 | 4/2007 | Amidon et al. |
| 2007/0196509 A1 | 8/2007 | Riman et al. |
| 2007/0225328 A1 | 9/2007 | Fritz et al. |
| 2007/0227063 A1 | 10/2007 | Dale et al. |
| 2007/0294939 A1 | 12/2007 | Spear et al. |
| 2008/0017272 A1 | 1/2008 | Isomura et al. |
| 2008/0046277 A1 | 2/2008 | Stamets |
| 2008/0047966 A1 | 2/2008 | Carson |
| 2008/0145577 A1* | 6/2008 | Bayer ............... B32B 5/16 428/35.6 |
| 2008/0234210 A1 | 9/2008 | Rijn et al. |
| 2008/0295399 A1 | 12/2008 | Kawai et al. |
| 2008/0296295 A1 | 12/2008 | Kords et al. |
| 2009/0107040 A1 | 4/2009 | Vandnhove |
| 2009/0111163 A1 | 4/2009 | Hoang et al. |
| 2009/0191289 A1 | 7/2009 | Lutz et al. |
| 2009/0241623 A1 | 10/2009 | Matano et al. |
| 2009/0246467 A1 | 10/2009 | Delantar |
| 2009/0272758 A1 | 11/2009 | Karwacki et al. |
| 2009/0307969 A1 | 12/2009 | Bayer et al. |
| 2009/0321975 A1 | 12/2009 | Schlummer |
| 2010/0101190 A1 | 4/2010 | Dillon |
| 2010/0158976 A1 | 6/2010 | O'Brien et al. |
| 2010/0159509 A1 | 6/2010 | Xu et al. |
| 2010/0199601 A1 | 8/2010 | Boldrini et al. |
| 2010/0227931 A1 | 9/2010 | Kuwano et al. |
| 2010/0243135 A1 | 9/2010 | Pepper et al. |
| 2010/0326564 A1 | 12/2010 | Isomura et al. |
| 2011/0094154 A1 | 4/2011 | Joaquin |
| 2011/0108158 A1 | 5/2011 | Huwiler et al. |
| 2011/0265688 A1 | 11/2011 | Kalisz et al. |
| 2011/0268980 A1 | 11/2011 | Kalisz et al. |
| 2011/0269209 A1 | 11/2011 | Rocco et al. |
| 2011/0269214 A1 | 11/2011 | Kalisz et al. |
| 2011/0306107 A1 | 12/2011 | Kalisz et al. |
| 2012/0000165 A1 | 1/2012 | Williams |
| 2012/0006446 A1 | 1/2012 | Isomura et al. |
| 2012/0060446 A1 | 3/2012 | Merz |
| 2012/0076895 A1 | 3/2012 | Kirejevas et al. |
| 2012/0115199 A1 | 5/2012 | Li et al. |
| 2012/0124839 A1 | 5/2012 | Kalisz et al. |
| 2012/0132314 A1 | 5/2012 | Weigel et al. |
| 2012/0135504 A1 | 5/2012 | Ross |
| 2012/0225471 A1 | 9/2012 | McIntyre et al. |
| 2012/0227899 A1 | 9/2012 | McIntyre et al. |
| 2012/0231140 A1 | 9/2012 | Hofmann et al. |
| 2012/0270031 A1 | 10/2012 | Guan et al. |
| 2012/0270302 A1 | 10/2012 | Bayer et al. |
| 2012/0315687 A1 | 12/2012 | Bayer et al. |
| 2013/0095560 A1 | 4/2013 | McIntyre et al. |
| 2013/0105036 A1 | 5/2013 | Smith et al. |
| 2013/0210327 A1 | 8/2013 | Corominas |
| 2013/0224840 A1 | 8/2013 | Bayer et al. |
| 2013/0274892 A1 | 10/2013 | Lelkes et al. |
| 2013/0309755 A1 | 11/2013 | McIntyre et al. |
| 2014/0038619 A1 | 2/2014 | Moulsley |
| 2014/0056653 A1 | 2/2014 | Scully et al. |
| 2014/0069004 A1 | 3/2014 | Bayer et al. |
| 2014/0093618 A1 | 4/2014 | Forgacs et al. |
| 2014/0120602 A1 | 5/2014 | Winiski et al. |
| 2014/0163142 A1 | 6/2014 | Zhang et al. |
| 2014/0173977 A1 | 6/2014 | Juscius |
| 2014/0186927 A1 | 7/2014 | Winiski et al. |
| 2014/0371352 A1 | 12/2014 | Dantin et al. |
| 2015/0033620 A1 | 2/2015 | Greetham et al. |
| 2015/0038619 A1 | 2/2015 | McIntyre et al. |
| 2015/0101509 A1 | 4/2015 | McIntyre et al. |
| 2015/0197358 A1 | 7/2015 | Larsen |
| 2015/0342138 A1 | 12/2015 | Bayer et al. |
| 2015/0342224 A1 | 12/2015 | Medoff |
| 2016/0002589 A1 | 1/2016 | Winiski |
| 2016/0073589 A1 | 3/2016 | McNamara et al. |
| 2016/0264926 A1 | 9/2016 | Winiski et al. |
| 2016/0355779 A1 | 12/2016 | Ross |
| 2017/0000040 A1 | 1/2017 | Bayer et al. |
| 2017/0028600 A1 | 2/2017 | McIntyre et al. |
| 2017/0071214 A1 | 3/2017 | Rehage |
| 2017/0218327 A1 | 8/2017 | Amstislavski et al. |
| 2017/0253849 A1 | 9/2017 | Miller et al. |
| 2017/0253852 A1 | 9/2017 | Bayer et al. |
| 2018/0014468 A1 | 1/2018 | Ross et al. |
| 2018/0148682 A1 | 5/2018 | Ross et al. |
| 2018/0282529 A1 | 10/2018 | Kaplan-Bie |
| 2018/0368337 A1 | 12/2018 | McIntyre et al. |
| 2019/0059431 A1 | 2/2019 | Kozubal et al. |
| 2019/0090436 A1 | 3/2019 | Betts et al. |
| 2019/0284307 A1 | 9/2019 | Chase et al. |
| 2019/0322997 A1 | 10/2019 | Schaak |
| 2019/0330668 A1 | 10/2019 | Kozubal et al. |
| 2019/0338240 A1 | 11/2019 | Carlton et al. |
| 2019/0357454 A1 | 11/2019 | Mueller et al. |
| 2019/0359931 A1 | 11/2019 | Mueller et al. |
| 2019/0390156 A1 | 12/2019 | Bayer et al. |
| 2020/0024577 A1 | 1/2020 | Carlton et al. |
| 2020/0025672 A1 | 1/2020 | Scullin et al. |
| 2020/0095535 A1 | 3/2020 | Kozubal et al. |
| 2020/0102530 A1 | 4/2020 | Winiski et al. |
| 2020/0146224 A1 | 5/2020 | Kaplan-Bie et al. |
| 2020/0157506 A1 | 5/2020 | Bayer et al. |
| 2020/0196541 A1 | 6/2020 | Ross et al. |
| 2020/0208097 A1 | 7/2020 | Winiski |
| 2020/0239830 A1 | 7/2020 | O'Brien et al. |
| 2020/0255794 A1 | 8/2020 | Amstislavski et al. |
| 2020/0268031 A1 | 8/2020 | Macur et al. |
| 2020/0270559 A1 | 8/2020 | Macur et al. |
| 2020/0392341 A1 | 12/2020 | Smith et al. |
| 2021/0017486 A1 | 1/2021 | Kozubal et al. |
| 2021/0127601 A9 | 5/2021 | Kaplan-Bie et al. |
| 2021/0317433 A9 | 10/2021 | Schaak |
| 2021/0348117 A9 | 11/2021 | Winiski |
| 2021/0401019 A1 | 12/2021 | Bayer et al. |
| 2022/0025318 A1 | 1/2022 | Gandia et al. |
| 2022/0142907 A1 | 5/2022 | Bayer et al. |
| 2022/0240557 A1 | 8/2022 | Kawabata et al. |
| 2022/0290199 A1 | 9/2022 | Greetham et al. |
| 2022/0295825 A1 | 9/2022 | Ghotra et al. |
| 2022/0298470 A1 | 9/2022 | Sayed et al. |
| 2022/0315881 A1 | 10/2022 | Macur |
| 2022/0333055 A1 | 10/2022 | Winiski et al. |
| 2022/0354068 A1 | 11/2022 | Carlton et al. |
| 2022/0354152 A1 | 11/2022 | Winiski et al. |
| 2022/0361424 A1 | 11/2022 | Mueller et al. |
| 2022/0386666 A1 | 12/2022 | Kawabata et al. |
| 2023/0013465 A1 | 1/2023 | Kaplan-Bie et al. |
| 2023/0016412 A1 | 1/2023 | Perry |
| 2023/0024708 A1 | 1/2023 | Kaplan-Bie et al. |
| 2023/0056666 A1 | 2/2023 | Winiski et al. |
| 2023/0219265 A1 | 7/2023 | McIntyre et al. |

FOREIGN PATENT DOCUMENTS

| | | |
|---|---|---|
| CN | 1358413 A | 7/2002 |
| CN | 1732887 A | 2/2006 |
| CN | 101248869 A | 8/2008 |
| CN | 101653081 A | 2/2010 |
| CN | 101743854 B | 2/2013 |
| CN | 103146585 A | 6/2013 |
| CN | 101892163 B | 7/2013 |
| CN | 103283482 B | 7/2014 |

(56) References Cited

FOREIGN PATENT DOCUMENTS

| | | |
|---|---|---|
| CN | 103396954 B | 11/2014 |
| CN | 104025909 B | 5/2016 |
| CN | 105961035 A | 9/2016 |
| CN | 106380166 A | 2/2017 |
| CN | 106635825 A | 5/2017 |
| CN | 106947702 A | 7/2017 |
| CN | 108249037 A | 7/2018 |
| CN | 108753624 A | 11/2018 |
| CN | 108934760 A | 12/2018 |
| CN | 109897394 A | 6/2019 |
| CN | 106613359 B | 1/2020 |
| CN | 111066577 A | 4/2020 |
| CN | 112225326 A | 1/2021 |
| CN | 112442449 A | 3/2021 |
| CN | 113501994 A | 10/2021 |
| CN | 108753625 B | 11/2021 |
| CN | 113692913 A | 11/2021 |
| CN | 114175968 A | 3/2022 |
| CN | 216106969 U | 3/2022 |
| CN | 114617025 A | 6/2022 |
| CN | 111990171 B | 7/2022 |
| CN | 115104479 A | 9/2022 |
| CN | 115181679 A | 10/2022 |
| EP | 0226292 A1 | 6/1987 |
| EP | 1312547 A1 | 5/2003 |
| EP | 2677030 A1 | 12/2013 |
| EP | 2735318 A1 | 5/2014 |
| EP | 2835058 A1 | 2/2015 |
| EP | 2875805 A1 | 5/2015 |
| EP | 2878340 A1 | 6/2015 |
| EP | 2485779 B1 | 2/2018 |
| EP | 3292769 A1 | 3/2018 |
| ES | 2497415 B1 | 4/2015 |
| FR | 3006693 A1 | 12/2014 |
| FR | 3071507 A1 | 3/2019 |
| GB | 142800 A | 1/1921 |
| GB | 1525484 A | 9/1978 |
| GB | 2032456 A | 5/1980 |
| GB | 2165865 A | 4/1986 |
| IN | 358266 B | 7/2020 |
| IN | 202111003691 A | 2/2021 |
| IN | 202141024595 A | 7/2021 |
| IN | 202031032279 A | 2/2022 |
| JP | S52066679 A | 6/1977 |
| JP | S55048388 A | 4/1980 |
| JP | H03234889 A | 10/1991 |
| JP | H049316 A | 1/1992 |
| JP | 2002104988 A | 4/2002 |
| JP | 2003526353 A | 9/2003 |
| JP | 2009519042 A | 5/2009 |
| JP | 2011130766 A | 7/2011 |
| JP | 2016512699 A | 5/2016 |
| JP | 6111510 B1 | 4/2017 |
| JP | 2023002897 A | 1/2023 |
| KR | 20050001175 A | 1/2005 |
| KR | 101569282 B1 | 11/2015 |
| KR | 101619664 B1 | 5/2016 |
| KR | 101851655 B1 | 4/2018 |
| KR | 102256335 B1 | 5/2021 |
| KR | 1020220138955 A | 10/2022 |
| KR | 102463058 B1 | 11/2022 |
| KR | 1020220163083 A | 12/2022 |
| KR | 1020220163084 A | 12/2022 |
| MX | 2017016725 A | 6/2019 |
| MY | 163845 A | 10/2017 |
| RU | 2716106 C1 | 3/2020 |
| WO | WO 1992/013960 | 8/1992 |
| WO | WO 1998/052403 | 11/1998 |
| WO | WO 1999/024555 | 5/1999 |
| WO | WO 2001/087045 | 11/2001 |
| WO | WO 2002/019798 | 3/2002 |
| WO | WO 2003/089506 | 10/2003 |
| WO | WO 2004/111181 | 12/2004 |
| WO | WO 2005/023323 | 3/2005 |
| WO | WO 2005/067977 | 7/2005 |
| WO | WO 2007/031129 | 3/2007 |
| WO | WO 2007/139321 | 12/2007 |
| WO | WO 2008/025122 | 3/2008 |
| WO | WO 2008/073489 | 6/2008 |
| WO | WO 2010/005476 | 1/2010 |
| WO | WO 2012/122092 | 9/2012 |
| WO | WO 2012/148995 | 11/2012 |
| WO | WO 2014/039938 | 3/2014 |
| WO | WO 2014/110539 | 7/2014 |
| WO | WO 2014/195641 | 12/2014 |
| WO | WO 2015/024751 | 2/2015 |
| WO | WO 2016/149002 | 9/2016 |
| WO | WO 2017/056059 | 4/2017 |
| WO | WO 2017/120342 | 7/2017 |
| WO | WO 2017/125602 A1 | 7/2017 |
| WO | WO 2017/132523 | 8/2017 |
| WO | WO 2017/136950 | 8/2017 |
| WO | WO 2017/151684 | 9/2017 |
| WO | WO 2017/205750 | 11/2017 |
| WO | WO 2018/011805 | 1/2018 |
| WO | WO 2018/014004 | 1/2018 |
| WO | WO 2018/064968 | 4/2018 |
| WO | WO 2018/183735 | 10/2018 |
| WO | WO 2018/189738 | 10/2018 |
| WO | WO 2019/046480 | 3/2019 |
| WO | WO 2019/099474 | 5/2019 |
| WO | WO 2019/178406 | 9/2019 |
| WO | WO 2019/217175 | 11/2019 |
| WO | WO 2019/226823 | 11/2019 |
| WO | WO 2019/237059 | 12/2019 |
| WO | WO 2019/246636 | 12/2019 |
| WO | WO 2020/023450 | 1/2020 |
| WO | WO 2020/072140 | 4/2020 |
| WO | WO 2020/082043 | 4/2020 |
| WO | WO 2020/082044 | 4/2020 |
| WO | WO 2020/102552 | 5/2020 |
| WO | WO 2020/106743 | 5/2020 |
| WO | WO 2020/176758 | 9/2020 |
| WO | WO 2020/186068 | 9/2020 |
| WO | WO 2020/186169 | 9/2020 |
| WO | WO 2020/237201 | 11/2020 |
| WO | WO 2021/092051 | 5/2021 |
| WO | WO 2021/144603 | 7/2021 |
| WO | WO 2022/079452 | 4/2022 |
| WO | WO 2022/091089 | 5/2022 |
| WO | WO 2022/135757 | 6/2022 |
| WO | WO 2022/157326 | 7/2022 |
| WO | WO 2022/189600 | 9/2022 |
| WO | WO 2022/195617 | 9/2022 |
| WO | WO 2022/200049 | 9/2022 |
| WO | WO 2022/212945 | 10/2022 |
| WO | WO 2022/265498 | 12/2022 |

OTHER PUBLICATIONS

Holt et al., "Biobased Composition Boards Made from Cotton Gin and Guayule Wastes: Select Physical and Mechanical Properties", Int J Mater Prod Tech. (2009) 36: 104-114.
Islam et al., "Morphology and mechanics of fungal mycelium", Scientific Reports, (2017) 7(1): 1-12.
Kerem et al., "Chemically defined solid-state fermentation of Pleurotus Ostreatus". Enzyme Microbiol Tech. (1993) 15(9): 785-790.
Kokubo et al., "Ca,P-rich layer formed on high-strength bioactive glass-ceramic A-W". J Biomed Mater Res. (1990) 24(3): 331-343.
Koutsoukos et al., "Precipitation of calcium carbonate in aqueous solutions". J Chem Soc., Faraday Trans. 1, Physical Chemistry in Condensed Phases, (1984) 80(5): 1181-1192.
Lu et al., "Theoretical Analysis of Calcium Phosphate precipitation in simulated Body Fluid". Biomaterials (2005) 26(10): 1097-1108—Pre-Pub. Version by Hong Kong University of Science and Technology, Department of Mechanical Engineering, Kowloon; 34 pages.
Molvinger et al., "Porous chitosan-silica hybrid microspheres as a potential catalyst". Chem Mater. (2004) 16(17): 3367-3372.
Monmaturapoj et al., "Influence of preparation method on hydroxyapatite porous scaffolds". Bull Mater Sci. (2011) 34(7): 1733-1737.
Manoli et al., "Crystallization of calcite on chitin". J Cryst Growth, (1997) 182(1-2): 116-124.

(56) References Cited

OTHER PUBLICATIONS

Mushroom Source, "Aspen Wood Shavings for Mushroom Cultivation", Website (2015) in 2 pages.
National Institute of Health (Nih/Nibib), "Tissue Engineering and Regenerative Medicine", Retrieved Sep. 24, 2018 from https://www.nibib.nih.gov/science-education/science-topics/tissue-engineering-and-regenerative-medicine in 13 pages.
Passauer U. et al., "Pilze in Höhlen" [Cave Mushrooms]. Denisia (2016) 37: 211-224.
Stewart B., "Concrete Fence Posts: Fact Sheet", Texas Agriculture Extension Service, Texas A & M University (1975) Article L-1368 in 4 pages.
Trinci et al., "II. Unrestricted Growth of Fungal Mycelia", The Mycota—Growth, Differenciation and Sexuality by Wessels et al. [Eds], Springer, Berlin, Heidelberg, (1994) Chapter II: 175-193.
Udawatte et al., "Solidification of xonotlite fibers with chitosan by hydrothermal hot pressing". J Mater Sci. Lttrs. (2000) 45(6): 298-301.
University of Sydney, "Competition Between Fungi". Webpage, accessed Jul. 16, 2014—http://bugs.bio.usyd.edu.au/learning/resources/Mycology/Ecology/competition.shtml in 3 pages.
Varma et al., "Porous calcium phosphate coating over phosphorylated chitosan film by a biomimetic method". Biomaterials (1999) 20(9): 879-884.
Wagner A. "Mycelium Biking—Eco-Design at its Best", Master's Thesis at Lulea University of Technology (2016) in 92 pages.
Woller R. "The Pearl Oyster Mushroom", University of Wisconsin Website (2011) in 2 pages.
Wan-Mohtar et al., "The morphology of Ganoderma lucidum mycelium in a repeated-batch fermentation for exopolysaccharide production", Biotechnology Reports (2016) 11: 2-11.
Weaver et al., "The stomatopod dactyl club: a formidable damage-tolerant biological hammer". Science (2012) 336(6086): 1275-1280.
Yamasaki et al., "A hydrothermal hot-pressing method: Apparatus and Application". J Mater Sci Lttrs. (1986) 5(3): 355-356.
Zivanovic et al., "Changes in Mushroom Texture and Cell Wall Composition Affected by Thermal Processing". J Food Service (2004) 69: 44-49.
Kuo, 2005-2006. Glossary of Mycological Terms. Mushroom Expert. Com., pp. 1-13; downloaded from http://www.mushroomexpert.com/glossary.html (May 8, 2015).
Gourmet Mushroom, Inc., "What is Mushroom?"—Mushroom Facts Mushroom Information—Educational & Science Projects (2004). Downloaded from www.gmushrooms.com, on Nov. 27, 2017; 5 pages.
Ross, P., "Pure Culture" 1997-Present; URL: <http://billhoss.phpwebhosting.com/ross/index.php?kind>; downloaded Dec. 14, 2016 in 11 pages.
Volk (2003) "Tom Volk's Fungus of the Month for Oct. 1998". This month's fungus is Pleurotus ostreatus; the Oyster mushroom, pp. 1-4, downloaded from http://botit.botany.wise.edu/toms_fungi/oct98.html on May 8, 2015.
Slater, M. "Young SoRo Entrepreneur Develops Environmentally Friendly Insulation." The Herald of Randolph. Jun. 21, 2007, pp. 1-2.
Thomas et al., "Growing Orchids in Perlite". In Perlite Plant Guide, The Schundler Company 1951, pp. 1-6, downloaded from http://www.schundler.com/index.html, archived on May 11, 2015.
Agnese et al., "Investigating the Influence of Various Plasticizers on the Properties of Isolated Films of Polyvinyl Acetat". The 37th Annual meeting and Exposition of the Controlled Release Society, Jul. 2010, Portland, OR U.S.A.
Amsellem et al., "Long-term preservation of viable mycelia of two mycoherbicidal organisms". Crop Protection (1999) 18: 643-649.
Angelini et al., "Effect of antimicrobial activity of Melaleuca alternifolia essential oil on antagonistic potential of Pleurotus species against Trichoderma harzianum in dual culture." World J Microbiol Biotech. (2008) 24(2): 197-202.

Antón et al., "PimM, a PAS Domain Positive Regulator of Pimaricin Biosynthesis in Streptomyces natalensis." Microbiol. (2007) 153: 3174-3183.
Appels et al., "Hydrophobin gene deletion and environmental growth conditions impact mechanical properties of mycelium by affecting the density of the material." Scientific Reports (2018) 8(1): 1-7.
Arshad et al., "Tissue engineering approaches to develop cultured meat from cells: a mini review." Cogent Food & Agriculture (2017) 3(1): 1320814 in 11 pages.
Ashiuchi et al., "Isolation of Bacillus subtilis (chungkookjang), a poly-gamma-glutamate producer with high genetic competence". Appl Microbiol Biotechnol. (2011) 57: 764-769.
Bajaj et al., "Poly (glutamic acid)—An emerging biopolymer of commercial interest". Bioresource Tech. (2011) 102(10): 5551-5561.
Baysal et al., "Cultivation of oyster mushroom on waste paper with some added supplementary materials". Biosource Technology (2003) 89: 95-97.
Begum et al., "Bioconversion and saccharification of some lignocellulosic wastes by Aspergillus oryzae ITCC-4857.01 for fermentable sugar production". Elect J Biotech. (2011) (14)5: 3 in 8 pages.
Belardinelli et al., "Actions of Adenosine and Isoproterenol on Isolated Mammalian Ventricular Myocytes." Circulation Res. (1983) 53(3): 287-297.
Belay et al., "Preparation and Characterization of Graphene-agar and Graphene Oxide-agar Composites." JOAPS (2017) 134(33): 45085.
Binder et al., "Phylogenetic and phylogenomic overview of the Polyporales". Mycologia (Nov.-Dec. 2013) 105(6): 1350-1373.
Blanchette et al., "Fungal mycelial mats used as textile by indigenous people of North America", Mycologia (Feb. 20, 2021) pp. 1-7.
Booth et al., "Potential of a dried mycelium formulation of an indigenous strain of Metarhizium anisopliae against subterranean pests of cranberry." Biocontrol Science and Technology (2000) 10: 659-668.
Bormann et al., "Characterization of a Novel, Antifungal, Chitin-binding Protein from Streptomyces Tendae Tü901 that Interferes with Growth Polarity." J Bacter. (1999) 181(24): 7421-7429.
Bowman et al., "The structure and synthesis of the fungal cell wall". Bioassays (2006) 28(8): 799-808.
Bružauskaite et al., "Scaffolds and Cells for Tissue Regernation: Different Scaffold Pore Sizes—Different Cell Effects." Cytotechnology (2016) 68(3): 355-369.
Byrd, "Clean meat's path to your dinner plate", The Good Food Institute, website accessed Nov. 14, 2018, https://www.gfi.org/clean-meats-path-to-commercialization; 11 pages.
Cerimi et al., "Fungi as source for new bio-based materials: a patent review", Fungal Biol Biotechnol. (2019) 6: 17; 10 pages.
Chai et al., "ß-Glucan Synthase Gene Overexpression and ß-Glucans Overproduction in Pleurotus ostreatus Using Promoter Swapping". PLoS ONE (2013) 8(4): e61693 in 7 pages.
Chaudhary et al., "Understanding rice hull ash as fillers in polymers: a review". Silicon Chemistry (2002) 1:281-289.
Chi et al., "Can Co-culturing of Two White-rot Fungi Increase Lignin Degradation and the Production of Lignin-degrading Enzymes?" Inter'l Biodeter Biodegrad. (2007) 59(1): 32-39.
Collins English Dictionary, "Mould", retrieved from http://collinsdictionary.com/dictionary/english/mould, archived on Apr. 8, 2015, 3 pages.
Dias et al., "Synthesis and characterization of chitosan-polyvinyl alcohol-bioactive glass hybrid membranes". Biomatter (2011) 1(1): 114-119.
Elleuche et al., "Carbonic anhydrases in fungi". Microbiology (2010) 156: 23-29.
Elsacker et al., "Growing living and multifunctional mycelium composites for large-scale formwork applications using robotic abrasive wire-cutting", Construction Bldg Mater. (2021) 283: 122732 in 16 pages.
Fleet G.H., "Cell walls", in The Yeasts, by Rose et al. [Eds.] 2nd Edition. vol. 4. London: Academic Press. (1991) pp. 199-277.

(56) References Cited

OTHER PUBLICATIONS

Frandsen R.J.N., "A guide to binary vectors and strategies for targeted genome modification in fungi using Agrobacterium tumefaciens-mediated transformation". J Microbiol Methods (2011) 87: 247-262.
Gardening KnowHow, Perlite Soil Info: Learn About Perlite Potting Soil, online at www.gardeningknowhow.com/garden-how-to/soil-fertilizers/perlite-potting-soil.htm downloaded on Dec. 16, 2015., 3 pages.
Glowacki et al., "Bioconjugation of Hydrogen-bonded Organic Semiconductors with Functional Proteins." J Mate Chem. C (2015) 3(25): 6554-6564.
Goodell et al., "Fungal Decay of Wood: Soft Rot-Brown Rot-white Rot". In Development of Commercial Wood Preservatives; Schultz et al. [Ed.] ACS Symposium Series; American Chemical Society, Washington, D.C. (2008), Chapter 2, pp. 9-31.
Google Report, Complete colonization substrate mushroom (2 pages) Jan. 30, 2018., 2 pages.
Google Dictionary Definition "Composite", downloaded on Nov. 21, 2018; 1 page.
Grant, James. J.—"An investigation of the airflow in mushroom growing structures, the development of an improved, three-dimensional solution technique for fluid flow and its evaluation for the modelling of mushroom growing structures", Doctoral Thesis Sep. 2002; 326 pages.
Greetham et al., "Pheotypic characterisation of Saccharomyces sensu stricto to Inhibitory Compounds Released During the Deconstruction of Lignocellulosic Material." 3th International Congress on Yeasts, ICY Aug. 26-30, 2012, Madison, USA; 1 page.
Griffin et al., "Regulation of macromolecular synthesis, colony development and specific growth rate of Achlya bisexualis during balanced growth". J General Microbiol. (1974) 80(2): 381-388.
Growers Supply. "Horticultural Coarse Perlite—4 Cubic Fee—Growers Supply". URL: https://growerssupply.com; Growers Supply 2012; www.growerssupply.com/farm/supplies/prod1:gs_growing_mediums:pg111049.html; downloaded Dec. 14, 2020 in 3 pages.
Haneef et al., "Advanced Materials from Fungal Mycelium: Fabrication and Tuning of Physical Properties", Scientific Reports 7(1): 1-11; DOI: 10.1038/srep41292, Jan. 24, 2017.
Heinzkill et al., "Characterization of laccases and peroxidases from wood-rotting fungi (family Coprinaceae)." Appl Environ Microbiol. (1998) 64: 1601-1606.
Heisig et al., USGS, "Ground-Water Resources of the Clifton Park Area, Saratoga County, New York", 2002, retrieved from the internet (Oct. 15, 2016): http://ny.water.usgs.gov/pubs/wri/wri014104/wrir01 -4104.pdf; 27 pages.
Home Depot "Miracle Gro® Perlite Mix", retrieved from the internet: http://homedepot.com/p/Miracle-Gro-8-pt-Perlite-Mix-74278430/204502291; 2 pages.
Home Depot "Pennington—Fast Acting Gypsum", retrieved from the internet: http://homedepot.com/p/Miracle-Gro-8-pt-Perlite-Mix-74278430/204502291; 2 pages.
Horton et al., "Regulation of Dikaryon-Expressed Genes by FRT1 in the Basidiomycete Schizophyllum commune". Fungal Genet Biol. (1999) 26(1): 33-47.
Howden et al., "The effects of breathing 5% CO2 on human cardiovascular responses and tolerance to orthostatic stress". Exper. Physiol. (2004) 89(4): 465-471.
Hüttner et al., "Recent advances in the intellectual property landscape of filamentous fungi", Fungal Biol Biotechnol. (2020) 7:16; 17 pgs.
Hyde et al., "The amazing potential of fungi: 50 ways we can exploit fungi industrially". Fungal Diversity (2019) 97(1): 1-136.
Instructables, How to Grow Oyster Mushroom Spawn (Low Tech), retrieved from the internet Aug. 19, 2018: http://www.instructables.com/id/1-How-to-Grow-Oyster-Mushroom-Spawn-Low-Tech/; 17 pages.
Jones et al., "Leather-like material biofabrication using fungi", Nature Sustainability (2020) https://doi.org/10.1038/s41893-020-00606-1, Sep. 7, 2020.

Kamzolkina et al., "Micromorphological features of Pleurotus pulmonarius (Fr.) Quel, and P. ostreaturs (Jacq.) P. Kumm. Strains in pure and binary culture with yeasts". Tsitologiia (2006) 48(2): 153-160.
Kemppainen et al., "Transformation of the Mycorrhizal Fungus Laccaria Bicolor using Agrobacterium tumefaciens." Bioengin Bugs (2011) 2(1): 38-44.
Kerem et al., "Effect of Mananese on Lignin Degradation by Pleurotus ostreatus during Solid-State Fermentation". Applied and Environmental Microbiology (1993) 59(12): 4115-4120.
Kilaru et al., "Investigating dominant selection markers for Coprinopsis cinerea: a carboxin resistance system and re-evaluation of hygromycin and phleomycin resistance vectors". Curr Genet. (2009) 55: 543-550.
Kim et al., "Current Technologies and Related Issues for Mushroom Transformation." Mycobiology (2015) 43(1): 1-8.
Kotlarewski et al., "Mechanical Properties of Papua New Guinea Balsa Wood." European J Wood Wood Products (2016) 74(1): 83-89.
Kück et al., "New tools for the genetic manipulation of filamentous fungi". Appl Microbiol Biotechnol. (2010) 86: 51-62.
Kües, U., "Life History and Development Processes in the Basidiomycete Coprinus Cinereus." Micro Molecular Biol Rev. (2000) 64(2): 316-353.
Kuhar et al., by Ingredi Potassium Sorbate vs Campden Tablets in Wine Making; Jun. 4, 2018. [online]; Retrieved from the Internet <URL: https://ingredi.com/blog/potassium-sorbate-vs-campden-tables-in-wine-making/>; 2 pages.
Li et al., "Preparation and Characterization of Homogeneous Hydroxyapatite/Chitosan Composite Scaffolds via In-Situ Hydration". J Biomaterials Nanobiotech. (2010) 1: 42-49.
Luo et al., "Coprinus comatus: a basidiomycete fungus forms novel spiny structures and infects nematode." Mycologia (2004) 96(6): 1218-1225.
McPherson et al., "Dissolvable Antibiotic Beads in Treatment of Periprosthetic Joint Infection and Revision Arthroplasty: The Use of Synthetic Pure Calcium Sulfate (Stimulan®) Impregnated with Vancomycin & Tobramycin." Reconstructive Review (2013) 3(1) 12 pages.
Merriam-Webster, "Chamber" dictionary definition; https://www.merriam-webster.com/dictionary accessed Jul. 10, 2017; in 4 Pages.
Merriam-Webster, "pack" Thesaurus definition; https://www.merriam-webster.com/thesaurus; synonyms accessed Aug. 19, 2019; in 10 Pages.
Michielse et al., "Agrobacterium-mediated Transformation of the Filamentous Fungus Aspergillus Awamori." Nature Protocols (2008) 3(10): 1671-1678.
Mitchell et al., [Eds.] "Solid-State Fermentation Bioreactors." Springer Verlag, Berlin/Heidelberg (2006); TOC in 12 Pages.
Moore D., "Fungal Morphogenesis." Cambridge University Press, Cambridge, UK; (1998) TOC in 8 Pages.
Moore D., "Tolerance of Imprecision in Fungal Morphogenesis." In Proceedings of the 4th Meeting on the Genetics and Cellular Biology of Basidiomycetes (Mar. 1998) pp. 13-19.
Mushroom Growers' Handbook 1, "Oyster Mushroom Cultivation". Part II, Chapter 5, (2005) pp. 75-85.
Mushroom Growers' Handbook 2, "Shiitake Bag Cultivation", Part I Shiitake. Published by Mush World (2005) Chapter 4, pp. 73-90 and pp. 105-109.
Naknean et al., "Factors Affecting Retention and Release of Flavor Compounds in Food Carbohydrates." Inter'l Food Res J. (2010) 17(1): 23-34.
Newaz et al., "Characterization of Balsa Wood Mechanical Properties Required for Continuum Damage Mechanics Analysis." Proceedings of the Institution of Mechanical Engineers, Part L: Journal of Materials: Design and Applications (2016) 230(1): 206-218.
Norvell L., Fungi Biology. Encyclopedia.(2002); 2 pages.
Novoselova et al., "Cocultivation of Pleurotus ostreatus (Jacq.) P. Kumm. with yeasts". Moscow University Biol Sciences Bulletin (2011) 66(3): 102-105.
Nussinovitch "Polymer Macro-and Micro-Gel Beads: Fundamentals and Applications", DOI 10.1007/978-1-4419-6618_2, Springer Science & Business Media LLC (2010) TOC in 8 Pages.

(56) References Cited

OTHER PUBLICATIONS

Paz et al., "One Step Contruction of Agrobacterium-Recombination-ready-plasmids (OSCAR): An Efficient and Robust Tool for ATMT Based Gene Deletion Construction in Fungi." Fungal Gen Biol. (2011) 48(7): 677-684.
Peksen et al., "Favourable Culture Conditions for mycelial growth of Hydnum repandum, a medicinal mushroom." African Journal of Traditional, Complementary and Alternative Medicines (2013) 10(6): 431-434.
Peng et al., "Microbial biodegradation of polyaromatic hydrocarbons". FEMS Microbiol Rev. (2008) 32:927-955.
Perez et al., "Myxococcus xanthus induces actinorhodin overproduction and aerial mycelium formation by Streptomyces coelicolor." Microbial Biotech. (2011) 4(2): 175-183.
Philippoussis et al., "Production of Mushrooms Using Agro-Industrial Residues as Substrates", in Biotechnology for Agro-Industrial Residues, Chapter 9, (2009) pp. 163-187.
Poppe J., Mushroom Growers' Handbook 1,2004, Part II. Chapter 5, "Substrate", pp. 80-81.
Pompei et al., "The Use of Olive Milling Waste-Water for the Culture of Mushrooms on Perlite". Acta Horticulturae (1994) 361:179-185.
Rai et al., "Production of Edible Fungi", in Fungal Biotechnology in Agricultural, Food, and Environmental Applications, D.K. Arora [Ed.], Marcel Dekker, Inc., (2003), Chapter 21, pp. 383-404.
Royse et al., "Influence of substrate wood-chip particle size on shiitake (Lentinula edodes) yield". Bioresource Tehnology (2001) 76(3): 229-233.
Sapak et al., "Effect of endophytic bacteria on growth and suppression of Tganoderma infection in oil palm". Int J Agric Biol. (2008) 10(2): 127-132.
Schaner et al., "Decellularized Vein as a Potential Scaffold for Vascular Tissue Engineering." J Vascular Surg. (2004) 40(1): 146-153.
Schirp et al., "Production and characterization of natural fiber-reinforced thermoplastic composites using wheat straw modified with the fungus Pleurotus ostreatus". J Appl. Polym Sci. (2006) 102:5191-5201.
Scholtmeijer et al., "Effect of introns and AT-rich sequences on expression of the bacterial hygromycin B resistance gene in the basidiomycete Schizophyllum commune". Appl Environ Microbiol. (2001) 67(1): 481-483.
Schuurman J., "Unique agar Pearls." YouTube video; Feb. 16, 2012, <https://www.youtube.com/watch?v=8GqTTOHETPQ>; 1 page.
Science Daily, May 7, 2007, retrieved from the Internet; http://www.sciencedaily.com/releases/2007/05/070506085628.htm., 3 pages.
Seamon K.B., "Forskolin: Unique Diterpene Activator of Adenylate Cyclase in Membranes and in Intact Cells." PNAS (1981) 78(6): 3363-3367.
Sinotech et al., (2015): retrieved from the Internet http://www.sinotech.com/compressionAndTransferMolding.html., 4 pages.
Staib et al., "Differential expression of the NRG1 repressor controls species-specific regulation of chlamydospore development in Candida albicans and Candida dubliniensis." Molecular Microbiol. (2005) 55(2): 637-652.
Stamets P., "Mycelium Running". Ten Speed Press (2005); pp. 18, 56, 58, 59, 85, 149, 157, 160 and 291 only.
Stamets P., "Growing Gourmet and Medicinal Mushrooms", (Undated) Chapter 21; p. 363.
Stanev et al., "Open Cell Metallic Porous Materials Obtained Through Space Holders. Part I: Production Methods, A Review". JMSE (2016) 139(5): 21 pages.
Stephens et al., "Bringing Cultured Meat to Market: Technical, Socio-political, and Regulatory Challenges in Cellular Agriculture." Trends in Food Science & Technology (2018) 78: 155-166.
Sundari et al., "Freeze-drying vegetative mycelium of Laccaria fraterna and its subsequent regeneration". Biotechnology Techniques (1999) 13:491-495.
Tartar et al., "Differential expression of chitin synthase (CHS) and glucan synthase (FKS) genes correlates with the formation of a modified, thinner cell wall in in vivo-produced Beauveria bassiana cells." Mycopathologia (2005) 160(4): 303-314.
Téllez-Jurado et al., "Expression of a heterologous laccase by Aspergillus niger cultured by solid-state and submerged fermentations." Enzyme Microbial Tech. (2006) 38(5): 665-669.
Téllez-Téllez et al., "Growth and laccase production by Pleurotus ostreatus in submerged and solid-state fermentation." Appl Microbiol Biotechnol. (2008) 81(4): 675-679.
Timberpress—"How Do Mushrooms Grow So Quickly.", downloaded from the internet: www.timberpress.com/blog/2017/01/how-do-mushrooms-grow-so-quickly, download Feb. 27, 2018 in 7 Pages.
Ugalde U., "Autoregulatory Signals in Mycelial Fungi" in The Mycota: A Comprehensive Treatise on Fungi as Experimental Systems for Basic and Applied Research. K. Esser [Ed.] Springer Publisher, 2nd Edition (2006) Chapter 11; pp. 203-213.
Universal Oil Field, "Sawdust", downloaded from universaloilfield.org on Aug. 23, 2018, 4 pages.
Vara et al., "Cloning and expression of a puromycin N-acetyl transferase gene from Streptomyces alboniger in Streptomyces lividans and *Escherichia coli*". Gene (1985) 33(22): 197-206.
Visser et al., "Pseudoxylaria as stowaway of the fungus-growing termite nest: Interaction asymmetry between Pseudoxylaria, Termitomyces and free-living relatives". Fungal Ecology (2011)4(5): 322-332.
Wang et al., "Influence of fungal elicitors on biosynthesis of natamycin by Streptomyces natalensis HW-2". Appl Microbiol Biothechnol. (2003) 97: 5527-5534.
Wikipedia, "Water gel (plain)", Wikipedia Contributors downloaded 2017-08-21 in 1 Page.
Wikipedia, "Wood", downloaded on Nov. 26, 2018, 1 page.
Xiao et al., "A Water-soluble Core Material for Manufacturing Hollow Composite Sections." Comp. Structures (2017) 182: 380-390.
Yang et al., "Medicinal Mushroom Ganoderma lucidum as a Potent Elicitor in Production of t-Resveratrol and t-Peceatannol in Peanut Calluses". J Agric Food Chem. (2010) 58(17): 9518-9522.
Zadrazil et al., "Influence of CO2 Concentration on the Mycelium Growth of Three Pleurotus Species", European J. Appl. Microbiol., vol. 1, pp. 327-335 (1975).
Zimin et al., "The MaSuRCA genome assembler". Bioinformatics (2013) 29(21): 2669-2677.
International Search Report and Written Opinion for PCT/US2007/025475, dated Jun. 24, 2008.
Bandalan et al., "Inhibitory effect of garlic (Allium sativum L.) against bread mold and its influence on the quality of yeast-leavened bread", Int J Food Engineer. (Dec. 2018) 4(4): 256-262.
Enrione et al., "Edible scaffolds based on non-mammalian biopolymers for Myoblast growth". Materials (Basel) (Dec. 2017) 10(12): 1404 in 15 pages.
Guan et al., "Construction and development of an auto-regulatory gene expression system in Bacillus subtilis". Microb Cell Fact Dec. 2015;14(1): 1-5.
Huang et al., "Genetically engineering Bacillus subtilis with a heat-resistant arsenite methyltransferase for bioremediation of arsenic-contaminated organic waste". Appl Enviro Microbiol. Oct. 1, 2015;81(19): 6718-6724.
Kumla et al., "Cultivation of Mushrooms and Their Lignocellulolytic Enzyme Production Through the Utilization of Agro-Industrial Waste". Molecules Jun. 2020;25(12): 2811 in 41 pages.
Phiillips E., "Lignocellulose-debrading Microbes Give Plants New Life", American Soc Microbil. (Mar. 25, 2022) 6 pages.
Voronin et al., "Carbon and Nitrogen Isotope Composition of the Wood of Pinus sylvestris, Betula pendula and Populus tremula". Paleonotal J., Dec. 2020;54(8): 819-824.
Abbadi et al., "Immunocytochemical identification and localization of lipase in cells of the mycelium of Penicillium cyclopium variety", Appl Microbial Biotechnol (1995) 42: 923-930.
Ando et al., "Cosmetic material for skin whitening—contains mushroom mycelium cultured matter and e.g. ginseng extract, chondroitin sodium sulphate and/or hyaluronic acid", WPI/THOMSON (Jan. 14, 1992), 1992(8): Accession #1992-062018; Abstract of JP4009316A; in 9 pages.

(56) References Cited

OTHER PUBLICATIONS

Antinori et al., "Advanced mycelium materials as potential self-growing biomedical scaffolds." Scientific reports (2021) 11(1): 1-14.
Attias et al., "Biofabrication of Nanocellulose-Mycelium Hybrid Materials", Adv Sustainable Syst. (2020) 5(2): 2000196 in 12 pages; Supporting Information in 7 pages.
Borrás et al., "Trametes versicolor pellets production: Low-cost medium and scale-up", Biochem Eng J. (2008) 42(1): 61-66.
Collins English Dictionary, "Cavity", Definition; retrieved on Nov. 8, 2021; 1 page.
Green et al., "Mechanical Properties of Wood", Forest Products Laboratory, 1999. in Wood Handbook—Wood as an engineering material. Gen Tech. Rep. FPL-GTR-113, Chapter 4 in 46 pages.
Hidayat et al., "Characterization of polylactic acid (PLA)/kenaf composite degradation by immobilized mycelia of Pleurotus ostreatus". Inter Biodeter Biodegrad. (2012) 71: 50-54.
Holt et al. "Fungal mycelium and cotton plant materials in the manufacture of biodegradable molded packaging material: Evaluation study of select blends of cotton byproducts." J Biobased Mater Bioenergy (2012) 6(4): 431-439.
Jiang et al., "Manufacturing of Natural Composites with a Mycelium Binder and Vacuum-infused Vegetable Oil-based Resins", Poster dated May 2014; 1 page.
Jiang et al., "Vacuum Infusion of Mycelium-Bound Biocomposite Preforms with Natural Resins", CAMX ExpoConference Proceedings, Oct. 13-16, 2014, 13 pages.
Jiang et al., "Bioresin Infused then Cured Mycelium-based Sandwich-structure Biocomposites: Resin Transfer Molding (RTM) Process, Flexural Properties, and Simulation." J Cleaner Production (2019) 207: 123-135.
Jones et al., "Mycelim Composites: A Review of Engineering Characteristics and Growth Kinetics", J Bionanoscience (2017) 11(4): 241-257.
Jones et al., "Waste-derived Low-cost Mycelium Composite Construction Materials with Improved Fire Safety", FAM (Fire and Materials) (2018) 42(7): 816-825.
Jones et al., Chitin-chitosan Thin Films from Microbiologically Upcycled Agricultural By-products. In 13th International Conference on the Mechanical Behaviour of Materials, Melbourne, Australia (Jun. 2019) p. 66; in 7 pages.
Kuhn et al., [Eds.] Cell Walls and Membranes in Fungi—An Introduction (Abstract) in Biochemistry of Cell Walls and Membranes in Fungi, Chapter 1, Springer Verlag Berlin/Heidelberg 1990, 2 pages.
Merriam-Webster, "desiccated" (Adj.) Definition; downloaded on Nov. 8, 2021; 1 page.
Meyer et al., "Comparison of the Technical Performance of Leather, Artificial Leather, and Trendy Alternatives." Coatings (Feb. 2021) 11(2): 226; 14 pages.
Pathway-27, "Beta-glucan", Aug. 2012, retrieved from http://http://www.pathway27.eu/topstory/beta-glucan/on Oct. 7, 2021 in 2 pages.
Vetchinkina et al., "Bioreduction of Gold (III) Ions from Hydrogen Tetrachloaurate..." Scientific Practical J Health Life Sciences No. 4, ISSN 22188-2268, (2013) pp. 51-56.
Wang et al., "Chemical and structural factors influencing enzymatic saccharification of wood from aspen, birch and spruce". Biomass Bioengin. (2018) 109: 125-134.
Williams, J. "Growth Industry", Financial Times Jan. 12, 2019 (Mogu—Radical by Nature); download from URL <: https://mogu.bio/growth-industry-financial-times-uk-article/> in 1 page.
Wösten et al., "How a fungus escapes the water to grow into the air", Current Biology. (1999) 9(2): 85-88.
Wösten et al., "Growing Fungi Structures in Space", ACT Research Category/Space Architecture; Noordwijk, The Netherlands (Oct. 15, 2018) in 17 pages.
Zeng Z., "Cosmetic composition for cleaning skin, comprises glossy ganoderma spores and collagens, content of glossy ganoderma spores in composition and content of collagens in composition", WPI/Thomson (Feb. 5, 2006) 7: Accession #2007-057767; Abstract of CN1732887A; in 11 pages.
Ziegler et al., "Evaluation of Physico-mechanical Properties of Mycelium Reinforced Green Biocomposites Made from Cellulosic Fibers", Appl Engin Agricult. (2016) 32(6): 931-938.
Bianchi et al., "Comparison between Allo-Kramer and Warner Bratzler Devices to Assess Rabbit Meat Tenderness", Italian J Animal Science (2007) 6(suppl): 749-751.
Boudaoud et al., "FibrilTool, an ImageJ plug-in to quantify fibrillar structures in rax microscopy images", Nature Protocols (2014) 9: 457-483.
Miller R.K., "Quality Characteristics", in Muscle Foods: Meat Poultry and Seafood Technology, Kinsman et al. [eds], Springer Science & Media, (Mar. 2013) Chapter 11, 37 pages.
OCDE—Organisation for Economic Co-operation and Development, Environment, Health and Safety Publications Series on the Safety of Novel Foods and Feeds, No. 26, Consensus Document on Compositional Considerations for New Varieties of Oyster Mushroom [*Pleurotus ostreatus*]: Key Food and Feed Nutrients, Antinutrients and Toxicants; Paris Nov. 2013, 42 pages.
Pacquette et al., "Simultaneous determination of chromium, selenium, and molybdenum in nutritional products by inductively coupled plasma/mass spectrometry: Single-laboratory validation", J of AOAC International (Jul. 2011) 94(4): 1240-1252.
Pang et al., "Facile fabrication of gradient density organic aerogel foams via density gradient centrifugation and UV curing in one-step", J Sol-Gel Sci Technol. (Nov. 2018) 85: 243-250.
Roshita et al.,"Effect of exposure to different colors light emitting diode on the yield and physical properties of grey and white oyster mushrooms", AIP Conference Proceedings (Nov. 2018) 2030(1): 020110 in 8 pages.
Silverman J., "Development and Testing of Mycelium-based Composite Materials for Shoe Sole Applications." Thesis Spring 2018; Retrieved from the Internet: URL: http://udspace.udel.edu/bitstream/handle/19716/23768/Silverman_udel_006M_13300.pdf?sequence=1&isAllowed=y; (Apr. 1, 2018); 99 pages.
Tapias et al., Decellularized scaffolds as a platform for bioengineered organs, Curr Opin Organ Transplant (Apr. 2014) 19(2): 145-152.
Yang et al., "Physical and mechanical properties of fungal mycelium-based biofoam", J Mater Civil Engin. (Jul. 2017) 29(7): 04017030 in 9 pages.
Zeigler et al., "The Origins of 168, W23, and other Bacillus subtilis Legacy Stains", J Bacter. (Nov. 2008) 190: 6983-6995.
Britannica, The Editors of Encyclopedia. "mold". Encyclopedia Britannica, Feb. 7, 2021, https://www.britannica.com/science/mold-fungus. 1 page.
Kim et al., "Effect of aeration and agitation on the production of mycelial biomass and exopolysaccharides in an enthomopahtogenic fungus Paecilomyces sinclairlii". Ltts Applied Microbiol. May 1, 2003;36(5): 321-326.
Lumb et al., "Metal Chelating Tendencies of Glutamic and Aspartic Acids". J Phys Chem., Jul. 1953;57(7): 690-693.
Magyar C., "11 Smart uses for sawdust around your home & garden". Rural Sprout, published Oct. 26, 2020, 19 pages.
Mitcheson et al., "Cultured adult cardiac myocytes: Future applications, culture methods, morphological and electrophysiological properties". Cardiovasc Res. (1998) 39: 280-300.
Peter et al., "High Terpene Pines: Transforming existing and enabling new forest biorefineries". 2013; 1 page.
PubMLST (Public databases for Molecular Typing and Microbial Genome Diversity), "Isolate Bacillus Subtilis ATCC 6051", retrieved Sep. 15, 2022 from PubMLST; 1 page.
Sansinenea et al., "Secondary Metabolites of Soil *Bacillus* spp."; Biotechnol Lett. (2011) 33: 1523-1538.
Wikipedia, "Soil". Downloaded on Sep. 14, 2022, 51 pages.
Wikipedia, "Compost". Downloaded on Sep. 14, 2022, 21 pages.
Hartl et al., "Fungal chitinases: diversity, mechanistic properties and biotechnological potential". Appl Microbiol Biotechnol. Jan. 2012;93: 533-543.
IFC Solutions. Natural Food Coloring. 2023; pp. 1-4.
Millipore Sigma Database Search "Chelators", 2023, pp. 1-4.

(56) References Cited

OTHER PUBLICATIONS

Wrona T., 10 Powerful Nutrients Found Only in Meat. Jun. 9, 2022. 20 pages.

ASTM International, "Standard Test Method for Tensile Properties of Plastics". Designation: D638-10, published Jun. 2010 in 16 pages.

Elsacker et al., "Mechanical, physical and chemical characterisation of mycelium-based composites with different types of lignocellulosic substrates". PLoS One. Jul. 22, 2019;14(7): e0213954 in 20 pages.

Elsoud et al., "Current trends in fungal biosynthesis of chitin and chitosan". Bull Nat'l Res Centre. Dec. 2019;43(1): 12 pages.

Fisher A., "Industrial-strength fungus—Densely packed rootlike fibers can do the job of Styrofoam, insulation and, yes, even bricks". TIME Feb. 8, 2010:1 page.

Insider Business, "How Mushrooms are Turned into Bacon and Styrofoam—World Wide Waste", Apr. 11, 2021; XP093055859; Retrieved from the Internet: URL:https://www.youtube.com/watch?v=uznXI8wrdag&t=325s&ab_channel=InsiderBusiness [retrieved on Jun. 20, 2023] in 4 pages.

Kadirgamar S., "Company Uses Mushrooms to Grow Plastic Alternatives". Oct. 17, 2017; downloaded from https://daily.jstor.org/daily-author/skanda-kadirgamar/ in 5 pages.

Kumar, M.N.V.R., "A review of chitin and chitosan applications". React Function Polymers. Nov. 1, 2000;46(1):1-27.

Valencia et al., "Synthesis and application of scaffolds of chitosan-graphene oxide by the freeze-drying method for tissue regeneration". Molecules. Oct. 16, 2018;23(10): 2651 in 16 pages.

* cited by examiner

METHOD OF FORMING A MYCOLOGICAL PRODUCT

This is a Division of U.S. Ser. No. 13/856,086, filed Apr. 3, 2013 which is a Division of U.S. Ser. No. 12/001,556, filed Dec. 12, 2007, now U.S. Pat. No. 9,485,917.

This invention claims the benefit of Provisional Patent Application No. 60/875,243 filed Dec. 15, 2006 and Provisional Patent Application No. 60/927,458 filed May 3, 2007, the contents of each being incorporated by reference herein.

This invention relates to a method of forming a mycological product.

BACKGROUND OF THE INVENTION

Materials are produced today using a range of processes ranging from time intensive outdoor growth and harvesting to energy intensive factory centric production. As demand for raw goods and materials rise, the associated cost of such materials rises. This places greater pressure on limited raw materials, such as minerals, ores, and fossil fuels, as well as on typical grown materials, such as trees, plants, and animals. Additionally, the production of many materials and composites produces significant environmental downsides in the form of pollution, energy consumption, and a long post use lifespan.

Conventional materials such as expanded petroleum based foams are not biodegradable and require significant energy inputs to produce in the form of manufacturing equipment, heat and raw energy.

Conventionally grown materials, such as trees, crops, and fibrous plants, require sunlight, fertilizers and large tracts of farmable land.

Finally, all of these production processes have associated waste streams, whether they are agriculturally or synthetically based.

Fungi are some of the fastest growing organisms known. They exhibit excellent bioefficiency, of up to 80%, and are adept at converting raw inputs into a range of components and compositions. Fungi are composed primarily of a cell wall that is constantly being extended at the tips of the hyphae. Unlike the cell wall of a plant, which is composed primarily of cellulose, or the structural component of an animal cell, which relies on collagen, the structural oligosaccharides of the cell wall of fungi relay primarily on chitin. Chitin is strong, hard substance, also found in the exoskeletons of arthropods. Chitin is already used within multiple industries as a purified substance. These uses include: water purification, food additives for stabilization, binders in fabrics and adhesives, surgical thread, and medicinal applications.

Given the rapid growth times of fungi, its hard and strong cellular wall, its high level of bioeffeciency, its ability to utilize multiple nutrient and resource sources, and, in the filamentous types, its rapid extension and exploration of a substrate, materials and composites, produced through the growth of fungi, can be made more efficiently, cost effectively, and faster, than through other growth processes and can also be made more efficiently and cost effectively then many synthetic processes.

Numerous patents and scientific procedure exists for the culturing of fungi for food production, and a few patents detail production methods for fungi with the intent of using its cellular structure for something other than food production. For instance U.S. Pat. No. 5,854,056 discloses a process for the production of "fungal pulp", a raw material that can be used in the production of paper products and textiles.

Accordingly, it is an object of the invention to provide method of producing a mycological product in an economical manner.

Briefly, the invention provides a method that uses the growth of hyphae, collectively referred to as mycelia or mycelium, to create materials composed of the fungi cellular tissue.

The method employs a step for growing filamentous fungi from any of the divisions of phylum Fungi. The examples that are disclosed focus on composites created from basidiomycetes, e. g., the "mushroom fungi" and most ectomycorrhizal fungi. But the same processes will work with any fungi that utilizes filamentous body structure. For example, both the lower fungi, saprophytic oomycetes, the higher fungi, divided into zygomycetes and endo-mycorrhizal fungi as well as the ascomycetes and deutoeromycetes are all examples of fungi that possess a filamentous stage in their life-cycle. This filamentous stage is what allows the fungi to extend through its environment creating cellular tissue that can be used to add structural strength to a loose conglomeration of particles, fibers, or elements.

These and other objects and advantages will become more apparent from the following detailed description taken in conjunction with the accompanying drawings wherein.

Figure 1:
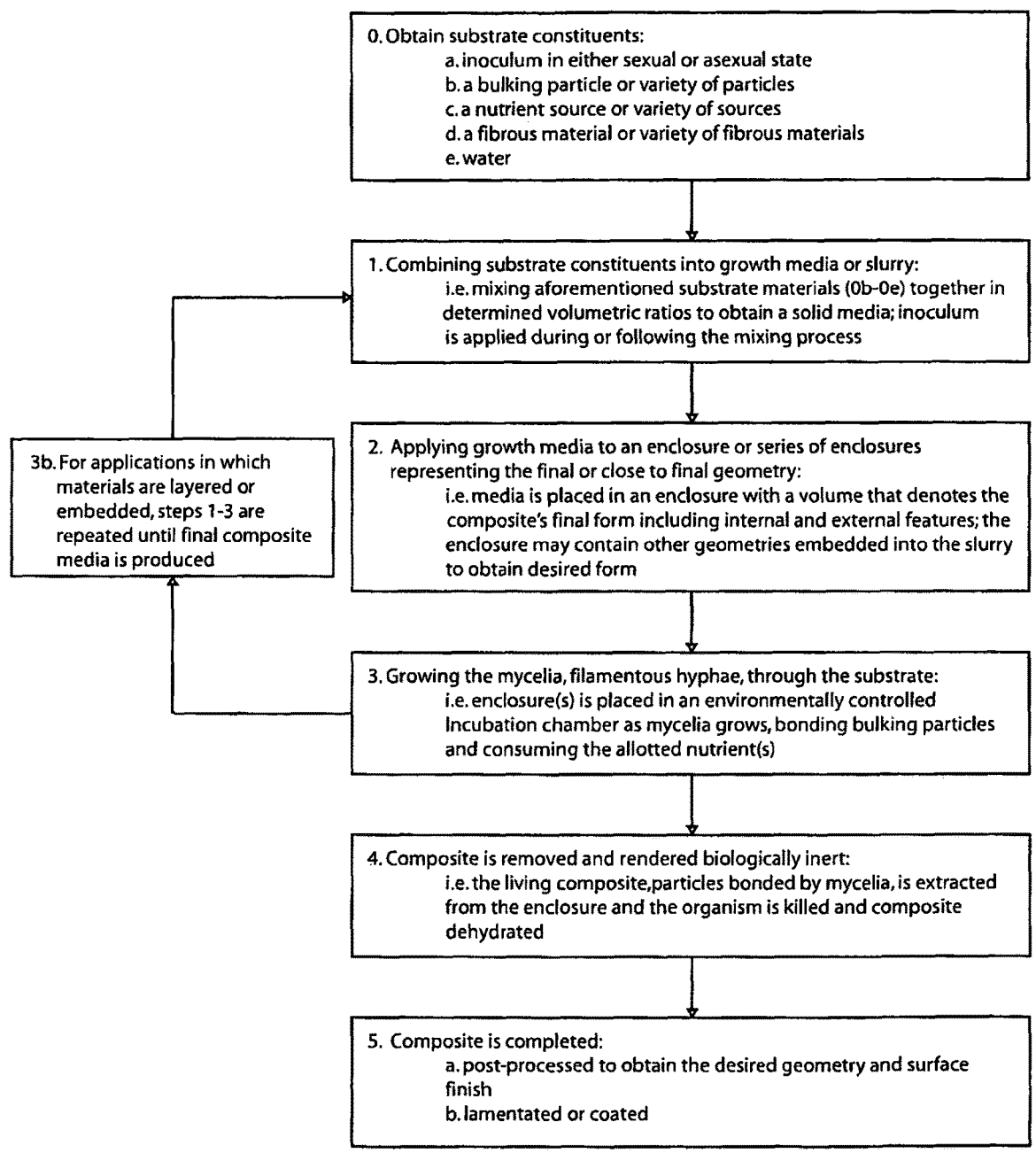
FIG. 1 illustrates a simplified flow chart of a method employed for making a fungi bonded material in accordance with the invention.

Referring to FIG. 1, the method of making a self-supporting structural material is comprised of the following steps.

0. Obtain substrate constituents, i.e. inoculum in either a sexual or asexual state, a bulking particle or a variety of bulking particles, a nutrient source or a variety of nutrient sources, a fibrous material or a variety of fibrous materials and water.

1. combining the substrate constituents into a growth media or slurry by mixing the substrate materials together in volumetric ratios to obtain a solid media while the inoculum is applied during or following the mixing process.

2. applying the growth media to an enclosure or series of enclosures representing the final or close to final geometry. The media is placed in an enclosure with a volume that denotes the composite's final form including internal and external features. The enclosure may contain other geometries embedded in the slurry to obtain a desired form.

3. growing the mycelia, i.e. filamentous hyphae, through the substrate. The enclosure is placed in an environmentally controlled incubation chamber as mycelia grows bonding the bulking particles and consuming the allotted nutrient(s).

3a. repeating steps 1-3 for applications in which materials are layered or embedded until the final composite media is produced.

4. removing the composite and rendering the composite biologically inert. The living composite, i.e. the particles bonded by the mycelia, is extracted from the enclosure and the organism is killed and the composite dehydrated.

5. completing the composite. The composite is post-processed to obtain the desired geometry and surface finish and laminated or coated.

The inoculum is produced using any one of the many methods known for the cultivation and production of fungi including, but not limited to, liquid suspended fragmented mycelia, liquid suspended spores and mycelia growing on solid or liquid nutrient.

Inoculum is combined with the engineered substrate, which may be comprised of nutritional and non-nutritional particles, fibers, or other elements. This mixture of inoculum and substrate is then placed in an enclosure.

In step 3, hyphae are grown through the substrate, with the net shape of the substrate bounded by the physical dimensions of the enclosure. This enclosure can take on any range of shapes including rectangles, boxes, spheres, and any other combinations of surfaces that produce a volume. Growth can occur both inside the enclosure and outside of the enclosure depending on desired end shape. Similarly, multiple enclosures can be combined and nested to produce voids in the final substrate. Other elements embedded with the slurry may also become integrated into the final composite through the growth of the hyphae.

The hyphae digest the nutrients and form a network of interconnected mycelia cells growing through and around the nutrients and through and around the non-nutrient particles, fibers, or elements. This growth provides structure to the once loose particles, fibers, elements, and nutrients, effectively bonding them in place while bonding the hyphae to each other as well.

In step 4, the substrate, now held tightly together by the mycelia network, is separated from the enclosure, and any internal enclosures or elements are separated away, as desired.

The above method may be performed with a filamentous fungus selected from the group consisting of ascomycetes, basidiomycetes, deuteromycetes, oomycetes, and zygomycetes. The method is preferably performed with fungi selected from the class: Holobasidiomycete.

The method is more preferably performed with a fungus selected from the group consisting of:
  Pleurotus ostreatus
  Agrocybe brasiliensis
  Flammulina velutipes
  Hypholoma capnoides
  Hypholoma sublaterium
  Morchella angusticeps
  Macrolepiota procera
  Coprinus comatus
  Agaricus arvensis
  Ganoderma tsugae
  Inonotus obliquus The method allows for the production of materials that may, in various embodiments, be characterized as structural, acoustical, insulating, shock absorbing, fire protecting, biodegrading, flexible, rigid, water absorbing, and water resisting and which may have other properties in varying degrees based on the selection of fungi and the nutrients. By varying the nutrient size, shape, and type, the bonded bulking particle, object, or fiber, size, shape, and type, the environmental conditions, and the fungi strain, a diverse range of material types, characteristics and appearances can be produced using the method described above.

The present invention uses the vegetative growth cycle of filamentous fungi for the production of materials comprised entirely, or partially of the cellular body of said fungi collectively known as mycelia.

Figure 2:
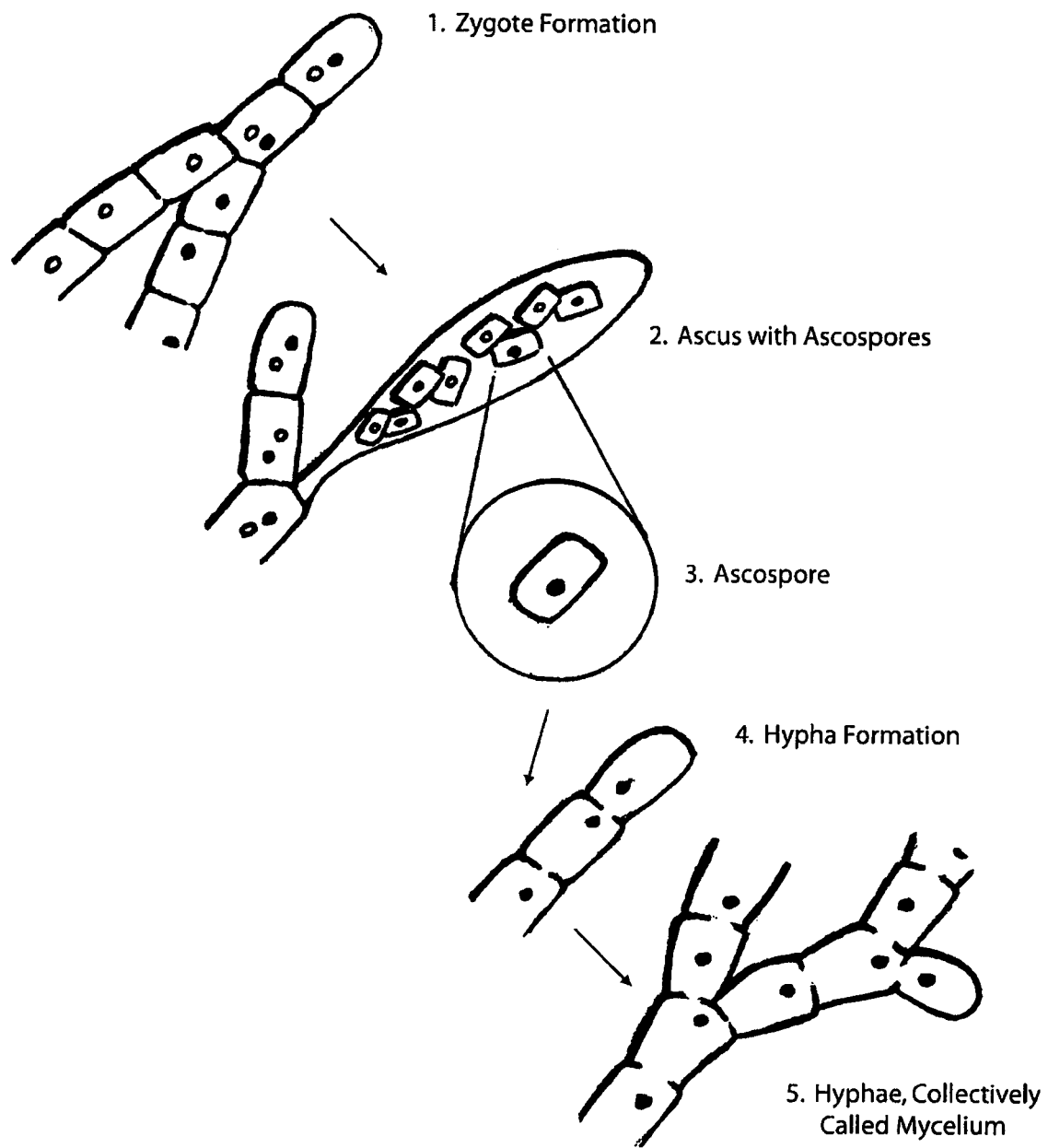
FIG. 2 illustrates a schematic life cycle of *Pleurotus ostreatus*.

FIG. 2 shows a schematic representation of the life cycle of *Pleurotus ostreatus*, filamentous fungi. The area of interest for this invention is the vegetative state of a fungi's life cycle where a fungi is actively growing through the extension of its tube like hyphae.

In this Description, the following definitions are specifically used:

Spore: The haploid, asexual bud or sexual reproducing unit, or "seed", of a fungus.

Hyphae: The thread-like, cellular tube of filamentous fungi which emerge and grow from the germination of a fungal spore.

Mycelium: The collection of hyphae tubes originating from a single spore and branching out into the environment.

Inoculum: Any carrier, solid, aerated, or liquid, of a organism, which can be used to transfer said organism to another media, medium, or substrate.

Nutrient: Any complex carbohydrate, polysaccharide chain, or fatty group, that a filamentous fungi can utilize as an energy source for growth.

Fruiting Body: A multicellular structure comprised of fungi hyphae that is formed for the purpose of spore production, generally referred to as a mushroom.

Fungi Culturing for Material Production
Methodology

Procedures for culturing filamentous fungi for material production.

All methods disclosed for the production of grown materials require an inoculation stage wherein an inoculum is used to transport a organism into a engineered substrate. The inoculum, carrying a desired fungi strain, is produced in sufficient quantities to inoculate the volume of the engineered substrates; inoculation volume may range from as low as 1% of the substrates total volume to as high as 80% of the substrates volume. Inoculum may take the form of a liquid carrier, solid carrier, or any other known method for transporting a organism from one growth supporting environment to another.

Generally, the inoculum is comprised of water, carbohydrates, sugars, vitamins, other nutrients and the fungi. Depending on temperature, initial tissue amounts, humidity, inoculum constituent concentrations, and growth periods, culturing methodology could vary widely.

Grown Material within an Enclosure

Figure 3:
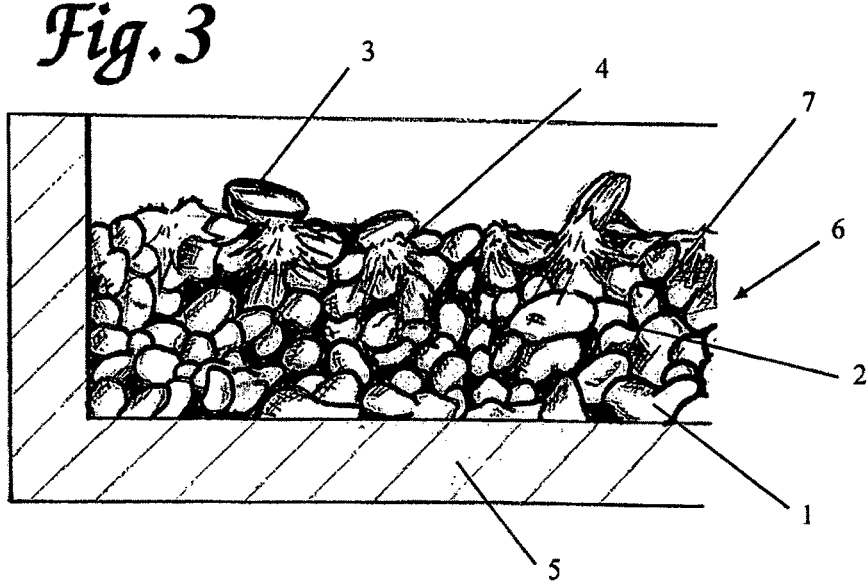
FIG. 3 illustrates an inoculated substrate before growth in an enclosure in accordance with the invention.

FIG. 3 shows a side view of one embodiment i.e. an insulating composite, just after inoculation has taken place.

In this embodiment, a group of nutritional particles 1 and a group of insulating particles 2 were placed in an enclosure 5 to form an engineered substrate 6 therein. The enclosure 5 has an open top and determines the final net shape of the grown composite. Thereafter, an inoculum 3 was applied directly to the surface of the engineered substrate 6.

Shortly after the inoculum 3 was applied to the surface, hyphae 4 were visible extending away from the inoculum 3 and into and around the nutritional particles 1 and insulating particles 2.

Figure 4:
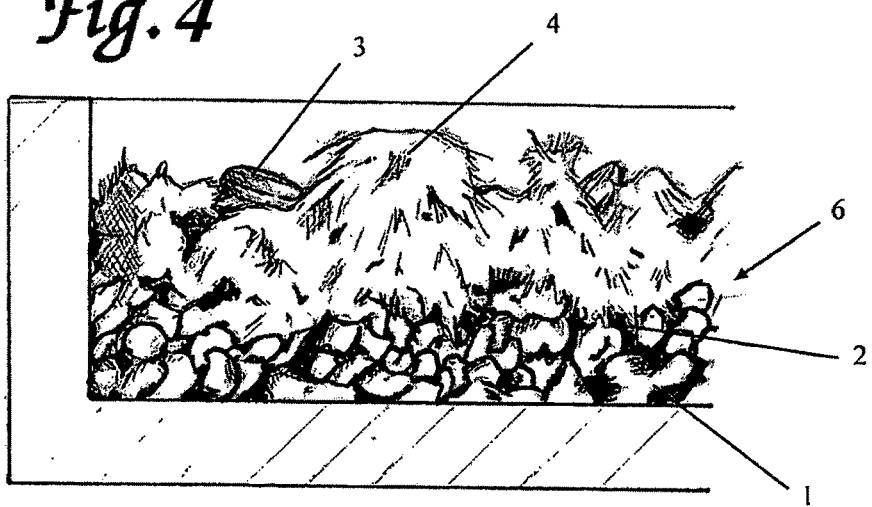
FIG. 4 illustrates an inoculated substrate after three days of growth in accordance with the invention.

FIG. 4 shows a side view of the same embodiment described above, i.e. an insulating composite, approximately 3 days after the inoculum 3 was applied to the surface of the engineered substrate 6. Hyphae 3 have now penetrated into the engineered substrate 6 and are beginning to bond insulating particles 2 and nutritional particles 1 into a coherent whole.

Figure 5:
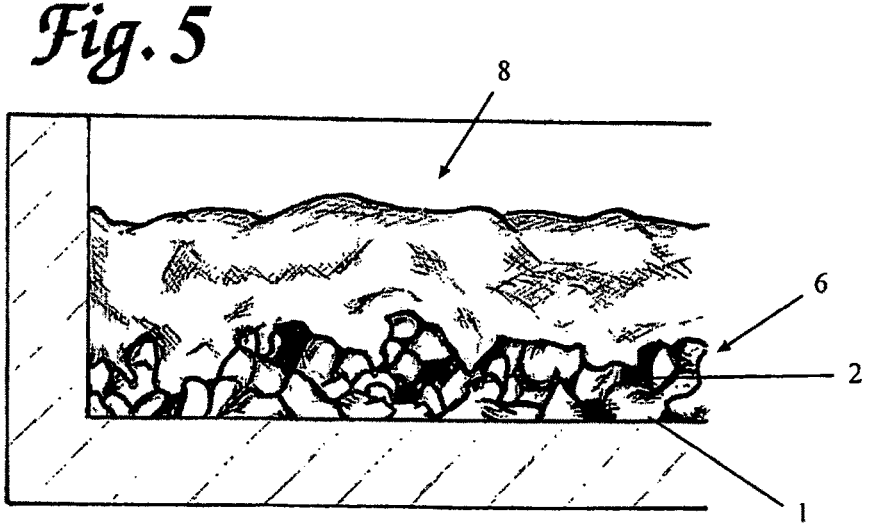
FIG. 5 illustrates an inoculated substrate nearing the end of the growth in accordance with the invention.

FIG. 5. shows a side view of the same embodiment of FIGS. 3 and 4, i.e. an insulating composite, approximately 7 days after the inoculum 3 was applied to the surface of the engineered substrate 6. Hyphae 3, collectively referred to as mycelia 7, have now fully colonized the top half of engineered substrate 6, bonding insulating particles 2 and nutritional particles 1 into a coherent whole.

Figure 6:
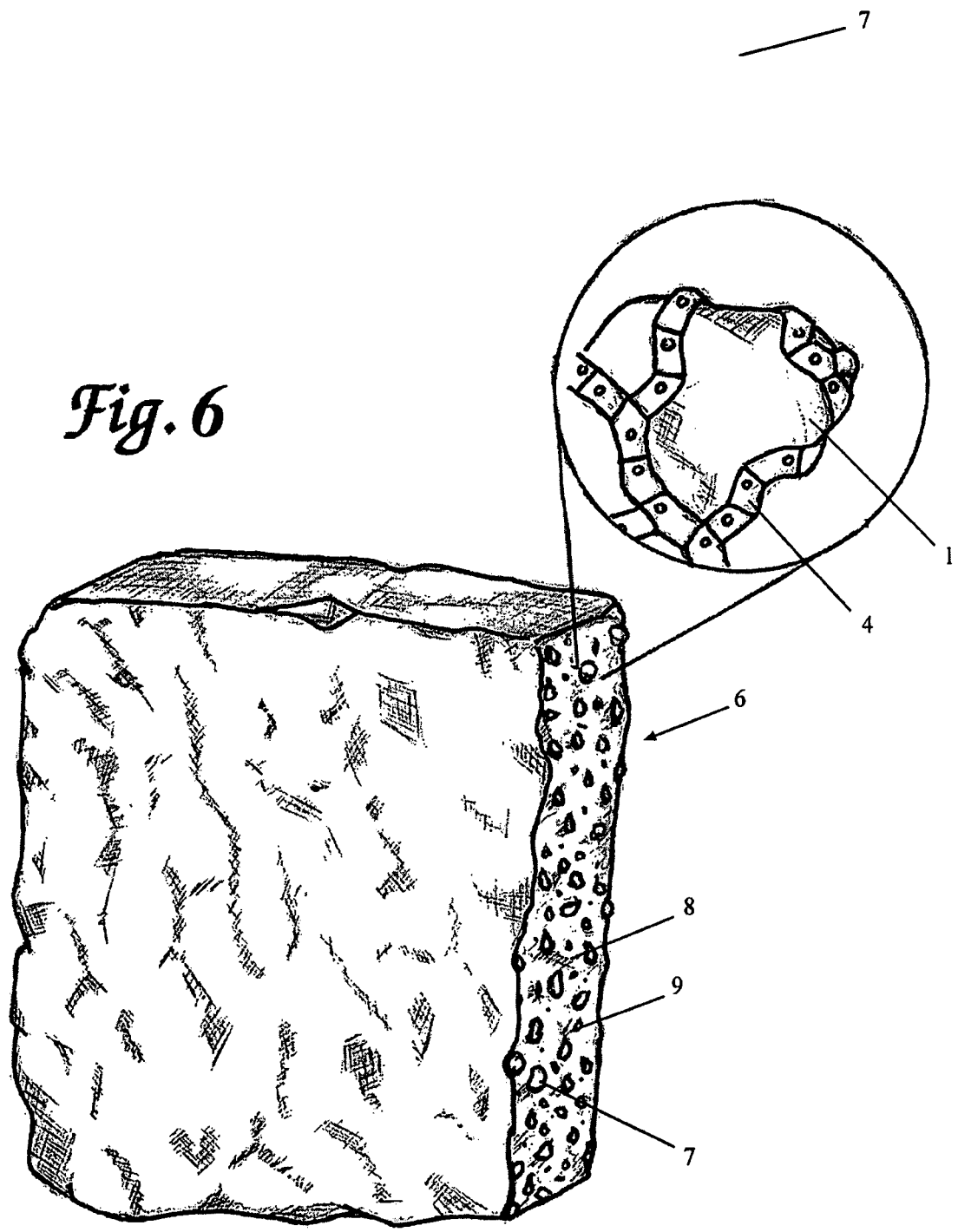
FIG. 6 illustrates a final composite of one embodiment composed of nutrient particles and a bulking particle in accordance with the invention.

FIG. 6 shows a side view of the same embodiments of FIGS. 3, 4 and 5, i.e. an insulating composite, after the engineered substrate 6 has been fully colonized and bonded by mycelia 7. A cutaway view shows a detail of a single insulating particle bound by a number of hyphae 4. Also shown within this embodiment are fibers 9 bound within mycelia 8.

Static Embodiment—Composite

FIG. 6 shows a perspective view of one embodiment of a mycelia bonded composite composed of nutritional particles, bulking particles, fibers, and insulating particles. In this embodiment of a mycelia bonded composite, the following growth conditions and materials were used: The engineered substrate was composed of the following constituents in the following percentages by dry volume:
1. Rice Hulls, purchased from Rice World in Arkansas, 50% of the substrate.
2. Horticultural Perlite, purchased from World Mineral of Santa Barbra, Calif., 15% of the substrate.
3. DGS, dried distillers grains, sourced from Troy Grain Traders of Troy N.Y., 10% of the substrate.
4. Ground cellulose, composed of recycled paper ground into an average sheet size of 1 mm×1 mm, 10% of the substrate.
5. Coco coir, sourced from Mycosupply, 10% of the substrate.
6. Inoculum composed of rye grain and inoculated with *Pleurotus ostreatus*, 3% of the substrate.
7. Birch sawdust, fine ground, 2% of the substrate by volume.
8. Tap water, from the Troy Municipal Water supply, was added until the mixture reached field capacity, an additional 30% of the total dry substrate volume was added in the form of water.

These materials were combined together in a dry mix process using a rotary mixer to fully incorporate the particles, nutrients, and fibers. Water was added in the final mixing stage. Total mixing time was 5 minutes.

The enclosures were incubated for 14 days at 100% RH humidity and at a temperature of 75° Fahrenheit. The enclosures serve as individual microclimates for each growing substrate set. By controlling the rate of gas exchange, humidity can be varied between RH 100%, inside an enclosure, and the exterior humidity, typically RH 30-50%. Each rectangular enclosure fully contained the substrate and inoculum preventing gaseous exchange. Opening the enclosures lids after 5 and 10 days allowed gaseous exchange. In some cases, lids included filter disks allowing continuous gas exchange.

After 14 days of growth, the enclosures were removed from the incubator. The loose fill particles and fibers having been bonded into a cohesive whole by the fungi's mycelium produced a rectangular panel with dimensions closely matching those of the growth enclosure. This panel was then removed from the enclosure by removing the lid, inverting the growth enclosure, and pressing gently on the bottom.

The mycelia bonded panel was then transferred to a drying rack within a convection oven. Air was circulated around the panel until fully dry, about 4 hours. Air temperature was held at 130 degrees Fahrenheit.

After drying, the now completed composite is suitable for direct application within a wall, or can be post processed to include other features or additions including water resistant skins, stiff exterior panel faces, and paper facings.

Within the above embodiment, the ratios and percentages of bulking particles, insulating particles, fibers, nutrients, inoculum, and water can be varied to produce composites with a range of properties. The materials expanded perlite compositions can vary from 5%-95% of the composite by volume. Other particles, including exfoliated vermiculite, diatomic earth, and ground plastics, can be combined with the perlite or substituted entirely. Particle sizes, from horticultural grade perlite to filter grade perlite are all suitable for composite composition and many different composite types can be created by varying the ratio of perlite particle size or vermiculite or diatomic earth particle size.

Rice hulls can compose anywhere from 5-95% of the composite material by volume. Fibers can compose from 1-90% of the material by volume. DGS can compose between 2-30% of the substrate by volume. The inoculum, when in the form of grain, can compose between 1-70% of the substrate by volume. The inoculum, when in other forms can comprise up to 100% of the substrate. Ground cellulose, sourced from waste paper, can compose from 1-30% of the substrate by volume.

Other embodiments may use an entirely different set of particles from either agricultural or industrial sources in ratios sufficient to support the growing of filamentous fungi through their mass.

Though not detailed in this embodiment, the engineered substrate can also contain elements and features including: rods, cubes, panels, lattices, and other elements with a minimum dimension 2 times larger than the mean diameter of the largest average particle size.

In this embodiment, the fungi strain *Pleurotus ostreatus* was grown through the substrate to produce a bonded composite. Many other filamentous fungi's could be used to produce a similar bonding result with differing final composite strength, flexibility, and water sorption characteristics.

In this embodiment, the substrate was inoculated using *Pleurotus ostreatus* growing on rye grain. Other methods of inoculation, including liquid spore inoculation, and liquid tissue inoculation, could be used with a similar result.

Incubation of the composite was performed at 100% RH humidity at 75° Fahrenheit. Successful incubation can be performed at temperatures as low as 35° Fahrenheit and as high as 130° Fahrenheit. RH humidity can also be varied to as low as 40%.

Drying was accomplished using a convection oven but other methods, including microwaving and exposing the composite to a stream of cool, dry air, are both viable approaches to moisture removal.

Figure 7:
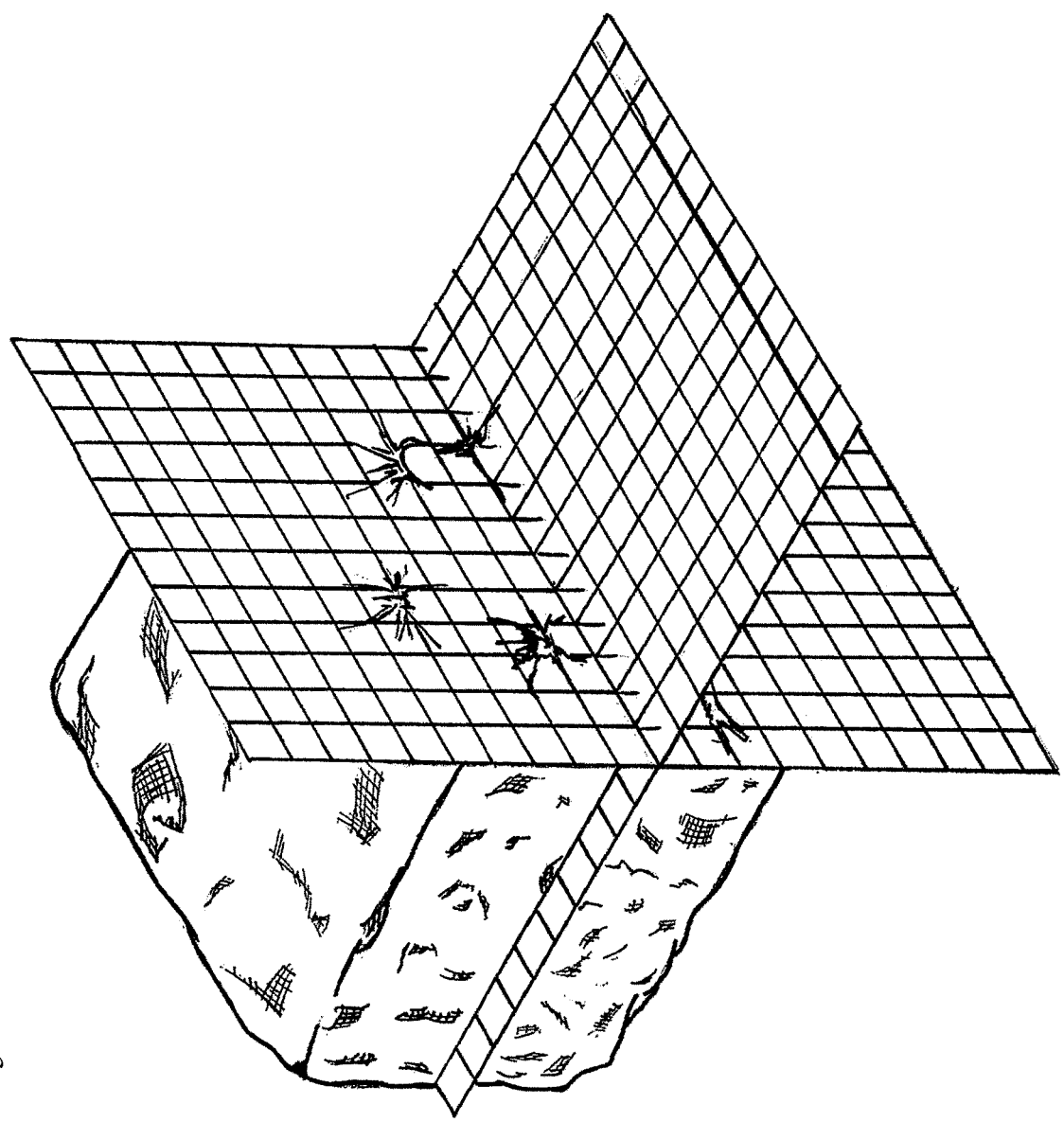
FIG. 7 illustrates a plastic lattice supporting mycelium growth in accordance with the invention.

Structure or Lattice for Mycelium Growth—FIG. 7

Mycelia based composites may be grown without the explicit use of a loose fill particle substrate. In fact, by creating a highly organized growth substrate, formations of mycelia composites can be created that might not normally arise when growth is allowed to propagate naturally through loose particles.

One way of adding an engineered structure to mycelium composites is to produce a digestible or non-digestible 3-d framework within which the mycelium grows. This framework may be formed from the group including: starch, plastic, wood, or fibers. This framework may be oriented orthogonally or oriented in other ways to produce mycelia growth primarily along the axis's of the grid. Additionally, this grid may be flexible or rigid. Spacing between grid members can range from 0.1 mm to upwards of 10 cm.

Growth along these engineered grids or lattices results in mycelium composites with highly organized hyphae strands allowing the design and production of composites with greater strength in chosen directions due to the organized nature of the supporting mycelia structure.

Such an arrangement also allows the development of organized mycelium structures composed primarily of hyphae rather than of bulking and nutritional particles.

To produce one embodiment of such a structure the following steps are taken:

Referring to FIG. 7, a three-dimensional lattice, formed of sets of 1 mm×1 mm plastic grids 14 oriented orthogonally, is coated in a mixture of starch and water. This mixture is composed of 50% starch, and 50% tap water by volume. These materials were sourced as organic brown rice flour, and tap water, from the Troy N.Y. municipal water supply, respectively.

This lattice is placed on/in a bed of inoculum containing *Pleurotus ostreatus* on a suitable nutrient carrier. The lattice and inoculum bed are then placed in an environment held at the correct temperature, between 55-95 degrees Fahrenheit, and humidity, between 75% RH and 100% RH, to stimulate mycelia growth.

FIG. 7 shows a cutaway of a grid based mycelium composite. Only two intersecting grids are shown, but the composite would actually be composed of a series of grids extending axially spaced 1 mm apart. Grid squares have an edge length of 1 mm. Here, mycelium 8 is shown growing through the grids 14. This thickly formed mycelia mat forms the bulk of the volume of the composite.

The mycelium is grown over and through the grid producing a dense network of oriented hyphae. Overtime, the hyphae will interweave producing a dense 3-D mat. After 1 to 2 weeks of growth, the grid is removed from the incubator and dried, using either a convection oven, or other means to remove the water from the mycelium mass. Once dried the mycelia composite can be directly used, or post processed for other applications.

Within this embodiment, the grid may or not provide the mycelia a nutrient source, but if nutrients are not provided within the grid framework, the grid must be placed in close proximity to an inoculum containing a nutrient source as to allow the fungi to transport nutrients into the grid based mycelium for further cellular expansion.

The invention thus provides a new method of producing grown materials. These materials may be flexible, rigid, structural, biodegradable, insulating, shock absorbent, hydrophobic, hydrophilic, non-flammable, an air barrier, breathable, acoustically absorbent and the like. All of the embodiments of this invention can have their material characteristics modified by varying the organism strain, nutrient source, and other particles, fibers, elements, or other items, included in the growth process.

Further, the invention provides a method of making a mycological material that can be used for various purposes, such as, for food production.

What is claimed is:

1. A method of forming a product comprising
providing a three-dimensional lattice having at least two grids oriented orthogonally to each other;
coating the lattice with a mixture of starch and water;
thereafter placing the lattice in a bed of inoculum containing *Pleurotus ostreatus* in a nutrient carrier;
thereafter stimulating mycelium growth over and through the grids of the lattice to produce a dense network of hyphae; and
allowing the hyphae to interweave over time to produce a mat of thickly formed mycelia on the lattice.

2. The method of claim 1, further comprising drying said mat.

3. The method of claim 1, wherein the stimulating mycelium growth comprises maintaining an environment at a temperature and a humidity sufficient to stimulate mycelium growth for a time period sufficient for the mycelium growth to form the dense network of hyphae.

4. The method of claim 3, wherein the dense network of hyphae is oriented on the lattice.

5. The method of claim 1, further comprising treating the mat by at least one of heating, irradiation, freezing, dehydration, and chemical treatment sufficient to kill the *Pleurotus ostreatus*.

6. The method of claim 1, further comprising placing the lattice and inoculum containing *Pleurotus ostreatus* in a cavity of predetermined shape, wherein the stimulating mycelium growth is carried out in the cavity whereby the resultant mat of thickly formed mycelia on the lattice adopts the shape of the cavity.

7. The method of claim 1, further comprising covering the lattice after adding the inoculum to prevent exposure of the inoculum to light.

8. The method of claim 1, wherein the nutrient carrier is at least one of a complex carbohydrate, a polysaccharide chain, and a fatty group capable of being used by a filamentous fungus as an energy source for growth.

9. The method of claim 1, wherein the mat comprises at least one exterior surface, and wherein the method further comprises bonding a veneer material to the at least one exterior surface of the mat.

10. The method of claim 9, wherein the veneer material is made of at least one of paper, oriented strand board, corrugated paper, and cardboard.

* * * * *